United States Patent [19]

Connor

[11] Patent Number: 4,548,744

[45] Date of Patent: Oct. 22, 1985

[54] ETHOXYLATED AMINE OXIDES HAVING CLAY SOIL REMOVAL/ANTI-REDEPOSITION PROPERTIES USEFUL IN DETERGENT COMPOSITIONS

[76] Inventor: Daniel S. Connor, The Proctor & Gamble Co., Miami Valley Laboratories, Cincinnati, Ohio 45247

[21] Appl. No.: 516,612

[22] Filed: Jul. 22, 1983

[51] Int. Cl.[4] .................. C07C 135/02; C08F 8/06; C11D 1/75

[52] U.S. Cl. .................. 252/545; 564/193; 564/201; 252/117; 564/202; 564/297; 252/524; 564/299; 252/526; 252/527; 252/528; 252/542; 252/546; 252/547; 260/404; 525/327.1; 525/328.2; 525/328.3; 525/328.4; 525/61; 525/417; 525/437; 525/460; 525/523; 528/341; 528/342; 528/347; 560/29; 560/103; 560/160; 560/170; 560/189; 560/222; 564/48; 564/59; 564/155; 564/159; 564/163

[58] Field of Search .............. 252/117, 524, 526, 527, 252/528, 542, 545, 546, 547, DIG. 15; 260/404; 525/327.1, 328.2, 328.4, 328.3, 435, 437, 417, 460, 523, 61; 528/341, 342, 347; 560/29, 103, 160, 170, 189, 222; 564/48, 59, 155, 159, 163, 193, 201, 202, 297, 299

[56] References Cited

U.S. PATENT DOCUMENTS

| | | | |
|---|---|---|---|
| 2,272,489 | 2/1942 | Ulrich | 260/239 E |
| 2,296,225 | 9/1942 | Ulrich | 260/239 R |
| 2,701,239 | 2/1955 | Ryznar | 252/321 |
| 2,778,814 | 1/1957 | Behrens et al. | 260/98 |
| 2,792,369 | 5/1957 | Dickson | 252/344 |
| 2,792,370 | 5/1957 | Dickson | 252/344 |
| 2,792,371 | 5/1957 | Dickson | 252/344 |
| 2,792,372 | 5/1957 | Dickson | 252/344 |
| 2,979,528 | 4/1961 | Lindsted | 564/505 |
| 3,040,076 | 6/1962 | Seidel et al. | 260/404 |
| 3,113,113 | 12/1963 | Marsh et al. | 252/392 |
| 3,154,489 | 10/1964 | Du Brow et al. | 252/8.75 |
| 3,178,366 | 4/1965 | Du Brow et al. | 252/8.8 |
| 3,200,106 | 8/1965 | Dickson et al. | 260/97.5 |
| 3,200,155 | 8/1965 | Kirkpatrick et al. | 564/504 |
| 3,236,671 | 2/1966 | Dybalski et al. | 106/277 |
| 3,294,695 | 12/1966 | Tippett | 252/149 |
| 3,301,783 | 1/1967 | Dickson et al. | 252/47.5 |
| 3,336,231 | 8/1967 | Marsh et al. | 252/546 |
| 3,398,197 | 8/1968 | Miller et al. | 564/504 |
| 3,412,155 | 11/1963 | Miller et al. | 564/297 |
| 3,418,374 | 12/1968 | Miller et al. | 564/504 |
| 3,444,200 | 5/1969 | Miller et al. | 564/282 |
| 3,457,312 | 7/1969 | Miller et al. | 564/297 |
| 3,473,919 | 10/1969 | Metcalfe et al. | 75/103 |
| 3,489,686 | 1/1970 | Parran | 252/106 |
| 3,492,352 | 1/1970 | Miller et al. | 564/374 |
| 3,494,962 | 2/1970 | Miller et al. | 564/299 |
| 3,510,521 | 5/1970 | Miller et al. | 564/504 |
| 3,523,088 | 8/1970 | Dean et al. | 252/539 |
| 3,549,542 | 12/1970 | Holderby | 252/524 |
| 3,549,546 | 12/1970 | Moore | 252/542 |
| 3,573,091 | 3/1971 | Waldman et al. | 252/8.8 |
| 3,580,853 | 5/1971 | Parran | 252/547 |
| 3,597,416 | 8/1971 | Diehl | 536/31 |
| 3,622,518 | 11/1971 | Atherton et al. | 252/357 |
| 3,671,305 | 6/1972 | Brown et al. | 428/272 |
| 3,671,502 | 6/1972 | Samour et al. | 526/287 |
| 3,684,427 | 8/1972 | Walz et al. | 8/590 |
| 3,719,647 | 3/1973 | Hardy et al. | 526/240 |
| 3,769,398 | 10/1973 | Hewitt | 424/70 |
| 3,833,378 | 9/1974 | Hayashi et al. | 430/268 |
| 3,838,057 | 9/1974 | Barnes et al. | 252/117 |
| 3,901,715 | 8/1975 | Callahan et al. | 106/2 |
| 3,925,262 | 12/1975 | Laughlin et al. | 252/526 |
| 3,929,678 | 12/1975 | Laughlin et al. | 252/526 |
| 3,936,503 | 2/1976 | Miller et al. | 564/286 |
| 4,000,091 | 12/1976 | Wentler | 252/524 |
| 4,000,092 | 12/1976 | Wentler | 252/526 |
| 4,071,428 | 1/1978 | Bosso et al. | 204/181 |

(List continued on next page.)

FOREIGN PATENT DOCUMENTS

| | | |
|---|---|---|
| 746953 | 11/1966 | Canada .................. 564/297 |
| 2085 | 5/1979 | European Pat. Off. . |
| 43,622 | 1/1982 | European Pat. Off. . |
| 1,298,077 | 6/1969 | Fed. Rep. of Germany . |
| 2,165,586 | 7/1973 | Fed. Rep. of Germany . |
| 2,165,900 | 7/1973 | Fed. Rep. of Germany . |
| 2,502,357 | 8/1975 | Fed. Rep. of Germany . |
| 2,843,645 | 4/1980 | Fed. Rep. of Germany . |
| 3,136,298 | 3/1983 | Fed. Rep. of Germany . |
| 7120-060 | 6/1971 | Japan . |
| 47-13013 | 4/1972 | Japan . |
| 47-13016 | 4/1972 | Japan . |
| 51-37260 | 10/1980 | Japan . |
| 7108-132 | 7/1982 | Japan . |
| 7108-133 | 7/1982 | Japan . |
| 75-08584 | 1/1976 | Netherlands . |
| 465,200 | 4/1937 | United Kingdom . |
| 718,010 | 2/1953 | United Kingdom . |
| 795,771 | 5/1958 | United Kingdom . |
| 825,676 | 12/1959 | United Kingdom . |
| 1,111,708 | 5/1968 | United Kingdom . |
| 1,296,352 | 11/1972 | United Kingdom . |
| 1,524,966 | 9/1978 | United Kingdom . |
| 1,563,599 | 3/1980 | United Kingdom . |
| 2,070,040 | 9/1981 | United Kingdom . |
| 562,568 | 7/1977 | U.S.S.R. . |

*Primary Examiner*—Dennis L. Albrecht

[57] ABSTRACT

Water-soluble ethoxylated amine oxides having clay soil removal/anti-redeposition properties are disclosed herein. These amine oxides are selected from ethoxylated monoamine oxides, ethoxylated diamine oxides, ethoxylated polyamine oxides, ethoxylated amine oxide polymers, and mixtures thereof. These amine oxides are useful at from about 0.05 to about 95% by weight in detergent compositions which further comprise from about 1 to about 75% by weight of a nonionic, anionic, ampholytic, zwitterionic, or cationic detergent surfactant or mixture thereof. In addition to these detergent surfactants, the detergent composition can optionally comprise from 0 to about 80% by weight of a detergent builder.

53 Claims, No Drawings

U.S. PATENT DOCUMENTS

| | | | |
|---|---|---|---|
| 4,101,690 | 7/1978 | Miyamoto et al. | 346/201 |
| 4,110,176 | 8/1978 | Creutz et al. | 204/52 |
| 4,118,324 | 10/1978 | Steckelberg et al. | 252/8.9 |
| 4,132,657 | 1/1979 | Verdiccio et al. | 252/32.5 |
| 4,134,970 | 1/1979 | Panka et al. | 424/70 |
| 4,138,371 | 2/1979 | Verdiccio et al. | 252/545 |
| 4,152,272 | 5/1979 | Young | 252/8.8 |
| 4,159,277 | 6/1979 | Gosselink et al. | 260/458 R |
| 4,165,334 | 8/1979 | Gosselink et al. | 260/458 R |
| 4,171,278 | 10/1979 | Andree et al. | 252/102 |
| 4,179,382 | 12/1979 | Rudkin et al. | 252/8.8 |
| 4,228,044 | 10/1980 | Cambre | 252/547 |
| 4,240,450 | 12/1980 | Grollier et al. | 132/7 |
| 4,301,044 | 11/1981 | Wentler et al. | 252/545 |
| 4,305,718 | 12/1981 | Löffler et al. | 8/532 |
| 4,313,895 | 2/1982 | Richmond et al. | 260/501.15 |
| 4,372,882 | 2/1983 | Koster et al. | 252/529 |
| 4,391,726 | 7/1983 | Kester | 252/99 |
| 4,394,305 | 7/1983 | Gosselink | 252/528 |
| 4,397,776 | 8/1983 | Ward | 252/527 |
| 4,415,488 | 11/1983 | Blaschke | 252/547 |
| 4,416,808 | 11/1983 | Blaschke | 252/547 |

ETHOXYLATED AMINE OXIDES HAVING CLAY SOIL REMOVAL/ANTI-REDEPOSITION PROPERTIES USEFUL IN DETERGENT COMPOSITIONS

TECHNICAL FIELD

The present application relates to amine oxides having clay-soil removal/anti-redeposition properties when used in detergent compositions.

A particularly important property of a detergent composition is its ability to remove particulate type soils from a variety of fabrics during laundering. Perhaps the most important particulate soils are the clay-type soils. Clay soil particles generally comprise negatively charged layers of aluminosilicates and positively charged cations (e.g. calcium) which are positioned between and hold together the negatively charged layers.

A variety of models can be proposed for compounds which would have clay soil removal properties. One model requires that the compound have two distinct characteristics. The first is the ability of the compound to adsorb onto the negatively charged layers of the clay particle. The second is the ability of the compound, once adsorbed, to push apart (swell) the negatively charged layers so that the clay particle loses its cohesive force and can be removed in the wash water.

One class of clay-soil removal compounds which appears to work according to this model are the polyethoxylated zwitterionic surfactants disclosed in U.S. Pat. No. 4,301,044 to Wentler et al., issued Nov. 17, 1981. Representative of such compounds are those having the formula:

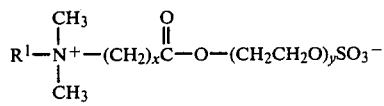

wherein $R^1$ is a $C_{14}-C_{20}$ alkyl group; x is 1 or an integer of from 3 to 5; and y is from 6 to 12. See also U.S. Pat. No. 3,929,678 to Laughlin et al., issued Dec. 30, 1975 (detergent composition containing polyethoxy zwitterionic surfactant plus other detergent surfactants); U.S. Pat. No. 3,925,262 to Laughlin et al., issued Dec. 9, 1975 (detergent composition containing polyethoxy zwitterionic surfactants with detergent builders); U.S. Pat. No. 4,157,277 to Gosselink et al., issued June 26, 1979 ($C_4$ polyoxyalkylene zwitterionic surfactants useful in detergent compositions); U.S. Pat. No. 4,165,334 to Gosselink et al., issued Aug. 21, 1979 (sulfonium-type polyethoxy zwitterionic surfactants).

These polyethoxy zwitterionic surfactants are generally compatible with other detergent surfactants such as the nonionic, zwitterionic and ampholytic types. However, as indicated in the Wentler et al. patent, most anionic surfactants interfere with the particulate soil removal performance of these compounds; anionic soils such as fatty acids likewise interfere. Because anionic detergent surfactants form the most important class of such materials for use in detergent compositions, the lack of compatibility between these polyethoxy zwitterionic surfactants and anionic surfactants poses a significant handicap where particulate (clay) soil removal is desired.

In addition to clay soil removal, one of the other properties mentioned in the Laughlin et al. patents with regard to these polyethoxy zwitterionic surfactants is the ability to keep the removed soil in suspension during the laundering cycle. Soil which is removed from the fabric and suspended in the wash water can redeposit onto the surface of the fabric. This redeposited soil causes a dulling or "graying" effect which is especially noticeable on white fabrics. Because soil is normally hydrophobic, this graying effect is a particularly important problem for those fabrics made in total or in part from hydrophobic fibers, e.g. polyester.

To minimize this problem, anti-redeposition or whiteness maintenance agents can be included in the detergent composition. Besides the previously mentioned polyethoxy zwitterionic surfactants, there are a variety of other compounds which can be used as anti-redeposition agents. One class of agents are the water-soluble copolymers of acrylic or methacrylic acid with acrylic or methacrylic acid-ethylene oxide condensates disclosed in U.S. Pat. No. 3,719,647 to Hardy et al., issued Mar. 6, 1973. Another class of anti-redeposition agents are the cellulose and carboxymethylcellulose derivatives disclosed in U.S. Pat. No. 3,597,416 to Diehl, issued Aug. 3, 1971 (ionic combination of dodecyltrimethyl phosphonium chloride and sodium carboxymethylcellulose), and U.S. Pat. No. 3,523,088 to Dean et al., issued Aug. 4, 1970 (anti-redeposition agent consisting of alkali metal carboxymethylcellulose and hydroxypropylcellulose). A mixture of compounds has also been used to provide not only anti-redeposition, but also clay soil removal properties. See U.S. Pat. No. 4,228,044 to Cambre, issued Oct. 14, 1980, which discloses detergent compositions having anti-redeposition and clay soil removal properties which can comprise a nonionic alkyl polyethoxy surfactant, a polyethoxy alkyl quaternary cationic surfactant and a fatty amide surfactant.

These anti-redeposition agents do have a number of significant handicaps. While effective to keep soil suspended, these compounds may lack additional clay soil removal properties. Moreover, as disclosed in the Diehl and Dean et al. patents, mixtures of compounds can be required to achieve the anti-redeposition benefit. To the extent that there are combined anti-redeposition/clay soil removal benefits as disclosed in the Cambre patent, mixtures of compounds are also required.

U.S. application Ser. No. 452,646 to J. M. Vander Meer filed Dec. 23, 1982, discloses detergent compositions which contain water-soluble ethoxylated amines having clay soil removal/anti-redeposition properties. These compounds are selected from ethoxylated monoamines, ethoxylated diamines, ethoxylated polyamines, ethoxylated amine polymers and mixtures thereof. It has been found that the clay soil removal/anti-redeposition benefits provided by these compounds decrease in the presence of standard chlorine (hypochlorite) bleaches. It would therefore be desirable to alter these compounds to make them more chlorine bleach compatible.

It is therefore an object of the present invention to provide compounds useful in detergent compositions which provide particulate soil, in particular clay soil, removal benefits.

It is a further object of the present invention to provide compounds useful in detergent compositions which provide clay soil removal benefits and are anionic detergent surfactant compatible.

It is yet another object of the present invention to provide compounds useful in detergent compositions having anti-redeposition properties.

It is yet a further object of the present invention to provide compounds useful in detergent compositions which combine both clay soil removal and anti-redeposition properties.

It is yet an additional object of the present invention to provide compounds useful in detergent compositions which are chlorine bleach compatible.

These and further objects of the present invention are hereinafter disclosed.

BACKGROUND ART

U.S. Pat. No. 3,457,312 to Miller et al., issued July 22, 1969, discloses alkoxylated amine oxides of secondary-alkyl and cycloalkylamines useful as detergents for dishwashing and shampooing, as surfactants, and as foam boosters. These amine oxides can have the formula:

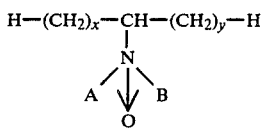

wherein A and B are polyethylene or polypropylene oxide moieties having from 1 to 50 oxyalkylene units; and x and y are integers having a sum of from 2 to 40. The compound N,N-bis(polyethoxylated[2–100 moles])-secondary-butylamine oxide is specifically disclosed. See also U.S. Pat. No. 3,494,962 to Miller et al., issued Feb. 10, 1970 (aryl-substituted aliphatic amine oxides which can have polyethoxy substituents on the nitrogen atom useful as surfactants and as components of shampoos and detergent formulations); Japanese Patent Document No. 7213-016 to Asaki Electro Chemical Co., published Apr. 20, 1972 (amine oxides useful as cleansing, defoaming, emulsifying, dispersing or softening agents produced by reaction of a halogenated polyoxyalkylene containing 5–90% oxyethylene units with a $C_1$–$C_3$ dialkyl substituted amine or $C_1$–$C_3$ trialkyl substituted ethylenediamine); Japanese Patent Document 7210-3013 to Asaki Electro Chemical Co., published Apr. 20, 1972 (amine oxides useful as detergents, bactericides, defoaming agents or lubricants produced by reaction of a sulfuric acid ester of a polyoxyalkylene glycol containing 10–90% oxyethylene units with a $C_1$–$C_3$ dialkyl substituted amine).

European Patent Application No. 42,188 to Koster, published Dec. 23, 1981, discloses detergent compositions having enhanced soil release and cleaning properties. These compositions contain from about 2 to about 60% by weight of a detergent surfactant and from 0.1 to 1.5% by weight of an amine oxide. This amine oxide has the formula:

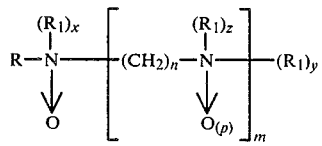

wherein R is $C_{10}$–$C_{22}$ alkyl or alkenyl; $R_1$ is $C_1$–$C_4$ alkyl, ethylene oxide or propylene oxide; n is from 1 to about 6; m is from 0 to about 6; and p is 0 or 1. Although x, y and z can each be from 1 to 10 with a total sum no greater than 25 when $R_1$ is ethylene oxide or propylene oxide, there is a preference that x, y or z should be no greater than 4 with a total sum of from 2 to 12. A particularly preferred class of amine oxides are those where $R_1$ is ethylene oxide; m is 1; n is 2 or 3; and x, y and z are each at least 1 with their sum being from 3 to 12. A preferred compound disclosed is N-hydrogenated $C_{16}$–$C_{18}$ tallow alkyl-N,N',N'-tri-(2-hydroxyethyl)-propylene-1,3-diamine oxide. See also U.S. Pat. No. 3,412,155 to Miller et al., issued Nov. 19, 1968 (fatty branched chain amine oxides useful as detergents, including ethoxylated amino stearyl amine dioxide); Japanese Patent Document No. 5137-260 to Nippon Oils and Fats, published Oct. 25, 1980 (desizing composition containing ethylene oxide/propylene oxide condensation product of an amine oxide of a $C_8$–$C_{22}$ alkyl alkylene diamine or a $C_{10}$–$C_{30}$ trialkyl amine).

DISCLOSURE OF THE INVENTION

The present invention relates to water-soluble ethoxylated amine oxides having clay soil removal/anti-redeposition properties. These compounds are selected from the group consisting of:

(1) ethoxylated monoamine oxides having formula I:

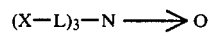

(2) ethoxylated amine oxides having formulas IIA, IIB or IIC:

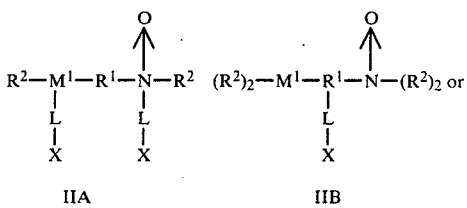

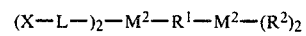

wherein $M^1$ is an

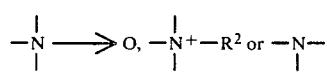

group; each $M^2$ is an

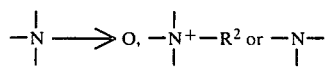

group, and at least one $M^2$ is an

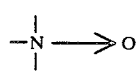

group;

(3) ethoxylated amine oxides having formula III:

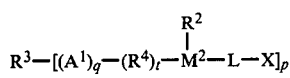

(4) ethoxylated amine oxide polymers which comprise a polymer backbone, at least 2 $M^3$ groups and at least one L—X group, wherein $M^3$ is an amine oxide group attached to or integral with the backbone; and L connects groups $M^3$ and X, or connects group X to the polymer backbone; and (5) mixtures thereof; wherein $A^1$ is

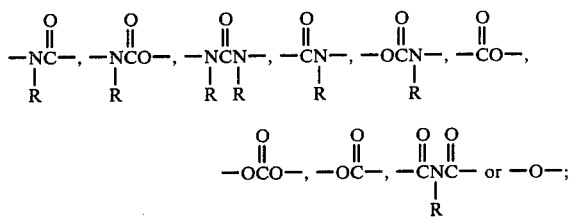

R is H or $C_1$-$C_4$ alkyl or hydroxyalkyl; $R^1$ is $C_2$-$C_{12}$ alkylene, hydroxyalkylene, alkenylene, arylene or alkarylene, or a $C_2$-$C_3$ oxyalkylene moiety having from 2 to about 20 oxyalkylene units provided that no O—N bonds are formed; each $R^2$ is $C_1$-$C_4$ alkyl or hydroxyalkyl, the moiety —L—X, or two $R^2$ together form the moiety —(CH$_2$)$_r$—$A^2$—(CH$_2$)$_s$—, wherein $A^2$ is —O— or —CH$_2$—, r is 1 or 2, s is 1 or 2 and r+s is 3 or 4; $R^3$ is a substituted $C_3$-$C_{12}$ alkyl, hydroxyalkyl, alkenyl, aryl or alkaryl group having p substitution sites; $R^4$ is $C_1$-$C_{12}$ alkylene, hydroxyalkylene, alkenylene, arylene or alkarylene, or a $C_2$-$C_3$ oxyalkylene moiety having from 2 to about 20 oxyalkylene units provided that no O—N bonds are formed; X is a nonionic group, or a mixture of nonionic and anionic groups; L is a hydrophilic chain which contains the polyoxyalkylene moiety —[($R^5$O)$_m$(CH$_2$CH$_2$O)$_n$]—, wherein $R^5$ is $C_3$-$C_4$ alkylene or hydroxyalkylene, and m and n are numbers such that the moiety —(CH$_2$CH$_2$O)$_n$— comprises at least about 50% by weight of said polyoxyalkylene moiety; n is at least about 12 for said monoamine oxides of formula I, is at least about 6 for said amine oxides of formulas IIA, IIB or IIC, and is at least 3 for said amine oxides of formula III and said amine oxide polymers; p is from 3 to 8; q is 1 or 0; t is 1 or 0, provided that t is 1 when q is 1.

The present invention further relates to detergent compositions which comprise from about 0.05 to about 95% by weight of these amine oxides or mixtures thereof. These detergent compositions further comprise from about 1 to about 75% by weight of a nonionic, anionic, ampholytic, zwitterionic, or cationic detergent surfactant, or mixture thereof. In addition to these detergent surfactants, the detergent compositions can optionally comprise from 0 to about 80% by weight of a detergent builder.

The amine oxides of the present invention provide clay soil removal benefits while being anionic detergent surfactant compatible. It is believed that the nitrogen atom of the amine oxide group causes adsorption of the compound onto the negatively charged layers of the clay particle. It is also believed that the hydrophilic ethoxy units attached to the compound swell the clay particle so that it loses its cohesive character and is swept away in the wash water. It is further believed that the oxidation of the nitrogen atom prevents undesirable interactions with chlorine (hypochlorite) bleach so that the compounds of the present invention are chlorine bleach compatible.

The anti-redeposition benefits provided by these amine oxides are also believed to be due to the nitrogen atom of the amine oxide group which cause it to be adsorbed onto soil suspended in the wash water. As more and more of these compounds adsorb onto the suspended soil, it becomes encased within a hydrophilic layer provided by the attached ethoxy units. As such, the hydrophilically encased soil is prevented from redepositing on fabrics, in particular hydrophobic fabrics such as polyester, during the laundering cycle.

Amine Oxides

In the preceding formulas IIA, IIB, and IIC, $R^1$ can be branched
(e.g.

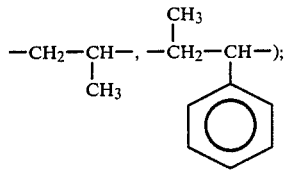

cyclic
(e.g.

or most preferably linear
(e.g. —CH$_2$CH$_2$—, —CH$_2$—CH$_2$—CH$_2$—,

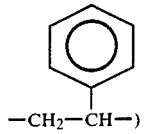

alkylene, hydroxyalkylene, alkenylene, alkarylene or oxyalkylene. $R^1$ is preferably $C_2$-$C_6$ alkylene. In the preceding formulas I, IIA, IIB, IIC and III, each $R^2$ is preferably methyl or most preferably the moiety —L—X.

In the preceding formulas I, IIA, IIB, IIC and III, X can be any compatible nonionic group, or mixture of nonionic and anionic groups. Suitable nonionic groups include $C_1$-$C_4$ alkyl or hydroxyalkyl ester or ether groups, preferably the acetate ester or methyl ether, respectively; hydrogen (H); or mixtures thereof. The particular preferred nonionic group is H. With regard to anionic groups, COO$^-$, PO$_3^{-2}$ and SO$_3^-$ are suitable. The preferred anionic group is SO$_3^-$. For preferred compounds, X is a nonionic group and preferably H.

In the preceding formulas I, IIA, IIB, IIC and III, hydrophilic chain L usually consists entirely of the polyoxyalkylene moiety —[($R^5$O)$_m$(CH$_2$CH$_2$O)$_n$]—. The moieties —($R^5$O)$_m$— and —(CH$_2$CH$_2$O)$_n$— of the polyoxyalkylene moiety can be mixed together or preferably form blocks of —(R⁵O)$_m$— and —(CH₂CH₂O)$_n$— moieties. R⁵ is preferably C₃H₆ (propylene); m is preferably from 0 to about 5 and is most preferably 0, i.e. the polyoxyalkylene moiety consists entirely of the moiety —(CH₂CH₂O)$_n$—. The moiety —(CH₂CH₂O)$_n$— preferably comprises at least about 85% by weight of the polyoxyalkylene moiety and most preferably 100% by weight (m is 0).

In the preceding formulas IIA, IIB IIC, and III, M¹ and each M² are preferably an

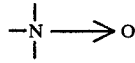

group. However, because oxidation of the

groups is sometimes not complete in the formation of the amine oxides, M¹ and M² can also be

groups. For improved bleach compatibility, it is desirable to minimize the number of these unoxidized

groups. For this purpose, all or some of the

groups remaining after oxidation can be quaternized to

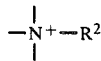

groups. Initially, some of the

groups can be quaternized to

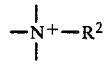

groups with the remaining unquaternized

groups being oxidized to

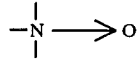

groups. The positive charge of these

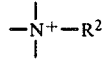

groups is offset by the appropriate number of counter anions. Suitable counter anions include Cl⁻, Br⁻, SO₃⁻², SO₄⁻², PO₄⁻³, MeOSO₃⁻ and the like. Particularly preferred counter anions are Cl⁻ and Br⁻.

Preferred ethoxylated mono- and diamine oxides (formulas I and IIA) have the formula I-II:

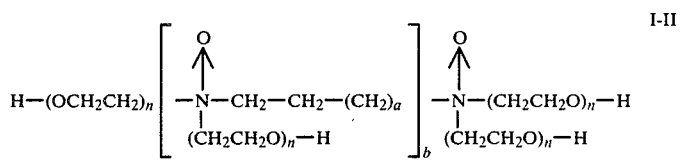

wherein n is defined as before; a is from 0 to 4 (e.g. ethylene, propylene, hexamethylene); b is 1 or 0. For preferred monoamine oxides (b=0), n is preferably at least about 15, with a typical range of from about 15 to about 35. For preferred diamine dioxides (b=1), n is at least about 12 with a typical range of from about 12 to about 42.

In the preceding formula III, R³ (linear, branched or cyclic) is preferably a substituted C₃–C₆ alkyl, hydroxyalkyl or aryl group; A¹ is preferably

n is preferably at least about 12, with a typical range of from about 12 to about 42; p is preferably from 3 to 6. When R³ is a substituted aryl or alkaryl group, q is preferably 1 and R⁴ is preferably C₂–C₃ alkylene. When R³ is a substituted alkyl, hydroxyalkyl, or alkenyl group, and when q is 0, R⁴ is preferably a C₂–C₃ oxyalkylene moiety; when q is 1, R⁴ is preferably C₂–C₃ alkylene.

These ethoxylated amine oxides of formula III (preferably polyamine oxides wherein three or more M² are

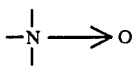

groups) can be

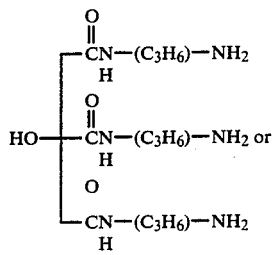

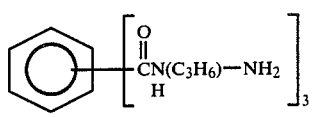

These ethoxylated amine oxides of formula III can also be derived from polyaminopropyleneoxide derivatives such as:

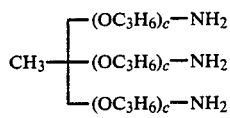

wherein each c is a number from 2 to about 20.

Methods for Making Amine Oxides

The mono-, di- and polyamine oxides of the present invention (compounds based on formulas I, IIA, IIB, IIC and III) can be prepared by standard methods for ethoxylating and oxidizing amines. There is preferably an initial step of condensing sufficient ethylene oxide to provide 2-hydroxyethyl groups at each reactive site (hydroxyethylation). This initial step can be omitted by starting with a 2-hydroxyethyl amine, e.g. triethanolamine (TEA). The appropriate amount of ethylene oxide is then condensed with these 2-hydroxyethylamines using an alkali metal (e.g., sodium, potassium), or a hydride or hydroxide thereof, as the catalyst to provide the respective ethoxylated amines. The total degree of ethoxylation per reactive site (n) can be determined according to the following formula:

Degree of Ethoxylation = $E/(A \times R)$ wherein E is the total number of moles of ethylene oxide condensed (including hydroxyethylation), A is the number of moles of the starting amine, and R is the number of reactive sites (typically 3 for the monoamines, 4 for diamines, and $2 \times p$ for polyamines) for the starting amine. The ethoxylated amine can then be oxidized with a strong oxidizing agent such as hydrogen peroxide to form the ethoxylated amine oxide.

Representative syntheses of mono- and diamine oxides of the present invention are as follows:

EXAMPLE 1

Step 1: Ethoxylation

Ethylenediamine (M.W. 60, 9.02 g., 0.15 moles) which had been dried over 3 Å molecular sieves was placed in a dry flask under dry argon. The flask was swept with ethylene oxide (EO) with rapid stirring. The temperature of the oil bath heating the flask was raised from 25° C. to 110° C. over a time period of 2.75 hrs. During this hydroxyethylation, 29.2 g. of EO was taken up for a degree of ethoxylation of 1.11.

A 40% KOH solution (2.9 g.) was added to the hydroxyethylated diamine and stirred under a vacuum for 1.25 hrs. at 110° C. to remove water. A 23 g. portion of this mixture was removed and the remainder (14.2 g., 0.056 moles) reacted with additional EO swept into the flask. The flask was heated by a 103°–122° C. temperature oil bath with moderately fast stirring for about 13 hrs. The resulting brown waxy solid had taken up 239.4 g. of EO for a total degree of ethoxylation of 25.3.

Step 2: Oxidation

The ethoxylated diamine from Step 1 (30.4 g., 0.0067 moles) and distilled water (30.5 ml.) were added together. This solutions was adjusted to pH 8 with 1N HCl. A 33.5% $H_2O_2$ solution (1.6 g., 0.016 moles) was then added. The reaction mixture was then heated with stirring for 15 hrs. in a 70° C. temperature water bath. More 33.5% $H_2O_2$ solution (0.07 g.) was then added to the reaction mixture. Stirring was continued at 65° C. for 2 hrs. Six ⅛″ alumina pellets impregnated with 0.5% platinum were added to the mixture which was permitted to stand at room temperature. See method disclosed in Swern, *Organic Peroxides,* Vol. I, (1970), p. 501. Complete destruction of $H_2O_2$ was evidenced by the cessation of oxygen gas evolution. The pellets were removed and the mixture was concentrated on a rotary evaporator to 80% ethoxylated diamine oxide assuming a yield of 30.6 g (0.0067 moles). Amine oxide analysis according to method of Brooks et al., *Anal. Chem.,* Vol. 31, (1959), p. 561 indicated that 71.4% of the tertiary amine groups had been oxidized.

EXAMPLE 2a

Step 1: Ethoxylation

To dried triethanolamine (TEA) (M.W. 17, 16.0 g., 0.11 moles) is is added 60% NaH in mineral oil (0.5 g., 0.013 moles). Ethylene oxide (EO) is then added under atmospheric pressure with stirring at 150°–170° C. After 23 hrs., 8.38 moles of EO is added to give a calculated total degree of ethoxylation of 26.1. The ethoxylated TEA is a light brown waxy solid.

Step 2: Oxidation

The ethoxylated TEA from step 1 (34.5 g., 0.01 moles) and distilled water (70 ml.) are placed in a flask. The solution is adjusted to pH 10 with 1N HCl. A 30% $H_2O_2$ solution (1.3 g., 0.011 mole equiv.) is added and the reaction mixture is then stirred at 65° C. for 6 hours. A dozen ⅛″ alumina pellets impregnated with 0.5% platinum are then added to the mixture which is permitted to stand at 65° C. with occasional stirring until a very low peroxide titration is obtained. This mixture containing the ethoxylated monoamine oxide can be concentrated to an 80% solution.

EXAMPLE 2b

Step 1: Ethoxylation 1,6-hexamethylenediamine (M.W. 116, 100 g., 0.86 moles) is placed in a flask and heated under argon to 85°

C. Ethylene oxide (EO) is bubbled into the flask. The reaction temperature is gradually raised to 120° C. over a time period of about 7.5 hours and is then raised briefly to 158° C. and is cooled back to 100° C. About 4 moles of EO are incorporated at this point.

Sodium spheres (1.24 g., 0.05 moles) are added and the reaction mixture is stirred overnight after which the sodium is consumed. The addition of EO is resumed and the reaction temperature is raised to 120° C. After about 3 hours, about 10 moles of EO are incorporated per mole of the diamine. An additional portion of sodium spheres (3.6 g., 0.15 moles) is added and ethoxylation is continued. The temperature is allowed to rise to 125°–130° C. Ethoxylation is continued for about 22 hours. The reaction is terminated when about 96 moles of EO is taken up per mole of the diamine to give a total degree of ethoxylation of about 24.

Step 2: Oxidation

The ethoxylated diamine from step 1 (43.4 g., 0.01 moles) and distilled water (87 ml.) are placed in a flask. The solution is adjusted to pH 10 with 1N HCl. A 30% $H_2O_2$ solution (2.5 g., 0.022 mole equiv.) is added and the reaction mixture is then stirred at 65° C. for 6 hours. A dozen ⅛″ alumina pellets impregnated with 0.5% platinum are added to the mixture which is permitted to stand at 65° C. with occasional stirring until a very low peroxide titration is obtained. This mixture containing the ethoxylated diamine oxide can be concentrated to an 80% solution.

Amine Oxide Polymers

The water-soluble amine oxide polymers of the present invention comprise a polymer backbone, at least 2 $M^3$ groups and at least one L—X group, wherein $M^3$ is an amine oxide group attached to or integral with the backbone; X is a nonionic group, or a mixture of nonionic and anionic groups; and L is a hydrophilic chain connecting groups $M^3$ and X, or connecting X to the polymer backbone.

As used herein, the term "polymer backbone" refers to the polymeric moiety to which groups $M^3$ and L—X are attached to or integral with. Included within this term are oligomer backbones (2 to 4 units), and true polymer backbones (5 or more units).

As used herein, the term "attached to" means that the group is pendent from the polymer backbone, examples of which are represented by the following general structures A and B:

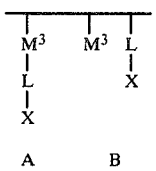

A    B

As used herein, the term "integral with" means that the group forms part of the polymer backbone, examples of which are represented by the following general structures C and D:

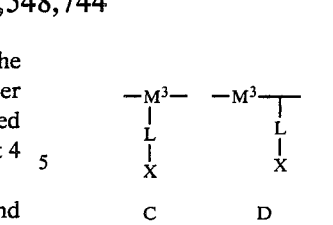

C    D

Any polymer backbone can be used as long as the amine oxide polymer formed is water-soluble and has clay soil removal/anti-redeposition properties. Suitable polymer backbones can be derived from the polyurethanes, the polyesters, the polyethers, the polyamides, the polyimides and the like, the polyacrylates, the polyacrylamides, the polyvinylethers, the polyethylenes, the polypropylenes and like polyalkylenes, the polystyrenes and like polyalkarylenes, the polyalkyleneamines, the polyalkyleneimines, the polyvinylamines, the polyallylamines, the polydiallylamines, the polyvinylpyridines, the polyaminotriazoles, polyvinyl alcohol, the aminopolyureylenes, and mixtures thereof.

$M^3$ can be any compatible amine oxide group which comprises an

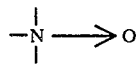

group. The

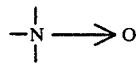

group can be represented by the following general structures E and F:

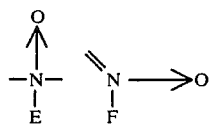

E    F

Particularly preferred $M^3$ groups are those containing an

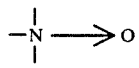

group represented by general structure E. The amine oxide group is preferably positioned close to or integral with the polymer backbone.

For the amine oxide polymers, X can be any compatible nonionic group, or mixture of nonionic and anionic groups. Suitable nonionic groups include $C_1$–$C_4$ alkyl or hydroxyalkyl ester or ether groups, preferably the acetate ester or methyl ether, respectively; hydrogen (H); or mixtures thereof. The particularly preferred nonionic group is H. With regard to anionic groups, $COO^-$, $PO_3^{-2}$ and $SO_3^-$ are suitable. The particularly preferred anionic group is $SO_3^-$. A mixture of from 0 to about 25% anionic groups and from 75 to 100% nonionic groups provides suitable clay soil removal/anti-redeposition properties. A mixture of from about 0 to about 10% anionic groups and from about 90 to 100% nonionic groups provides the preferred properties. Most preferably, X is 100% nonionic groups which are preferably H.

The amine oxide polymers of the present invention normally have a ratio of amine oxide groups $M^3$ to groups X of 1:1. However, for example, by appropriate copolymerization of tertiary amine group containing monomers and L—X group containing monomers, and/or oxidation of the resulting polymer to form the amine oxide groups, the ratio of amine oxide groups $M^3$ to groups X can be varied. The ratio of groups $M^3$ to groups X can usually range from about 2:1 to about 1:10. In preferred amine oxide polymers, the ratio is from about 1:1 to about 1:5. The polymers formed from such copolymerization are typically random, i.e. the monomers copolymerize in a nonrepeating sequence.

The units which contain groups $M^3$ and groups L—X can comprise 100% of the amine oxide polymers of the present invention. However, inclusion of other units in the polymers is also permissible. Examples of other units include acrylamides, vinyl ethers, and those containing unquaternized or quaternized tertiary amine groups (M') having an

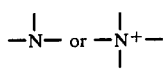

group, respectively. (The positive charge of the

groups is offset by the appropriate number of counter anions such as $Cl^-$, $Br^-$, $SO_3^{-2}$, $SO_4^{-2}$, $PO_4^{-3}$, $MeOSO_3^-$ and the like. For improved bleach compatibility, the number of

groups is desirably minimized.) These other units can comprise from 0 to about 90% of the polymer (from about 10 to 100% of the polymer being units containing $M^3$ and L—X groups, including M'—L—X groups). Normally, these other units comprise from 0 to about 50% of the polymer (from about 50 to 100% of the polymer being units containing $M^3$ and L—X groups).

The number of groups $M^3$ and L—X each usually ranges from about 2 to about 200. Typically, the number of groups $M^3$ and L—X are each from about 3 to about 100. Preferably, the number of groups $M^3$ and L—X are each from about 3 to about 40.

Other than moieties for connecting groups $M^3$ and X, or for attachment to the polymer backbone, hydrophilic chain L usually consists entirely of the polyoxyalkylene moiety —[($R^5O$)$_m$($CH_2CH_2O$)$_n$]—. The moieties —($R^5O$)$_m$— and —($CH_2CH_2O$)$_n$— of the polyoxyalkylene moiety can be mixed together, or preferably form blocks of —($R^5O$)$_m$— and —($CH_2CH_2O$)$_n$— moieties. $R^5$ is preferably $C_3H_6$ (propylene); m is preferably from 0 to about 5, and most preferably 0, i.e. the polyoxyalkylene moiety consists entirely of the moiety —($CH_2C$-$H_2O$)$_n$—. The moiety —($CH_2CH_2O$)$_n$— preferably comprises at least about 85% by weight of the polyoxyalkylene moiety, and most preferably 100% by weight (m is 0). For the moiety —($CH_2CH_2O$)$_n$—, n is usually from about 3 to about 100. Preferably, n is from about 12 to about 42.

A plurality (2 or more) of moieties —L—X can also be hooked together and attached to group $M^3$ or to the polymer backbone, examples of which are represented by the following general structures G and H:

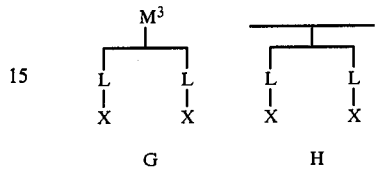

Structures such as G and H can be formed, for example, by reacting glycidol with group $M^3$ or with the polymer backbone, and ethoxylating the subsequently formed hydroxy groups.

Representative classes of amine oxide polymers of the present invention are as follows:

A. Polyurethane, Polyester, Polyether, Polyamide or Like Polymers

One class of suitable amine oxide polymers are derived from polyurethanes, polyesters, polyethers, polyamides and the like. These polymers comprise units selected from those having formulas IV, V and VI:

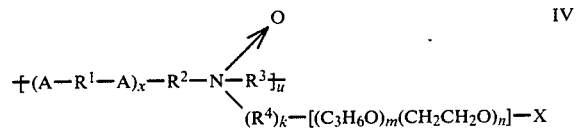

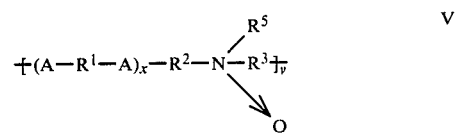

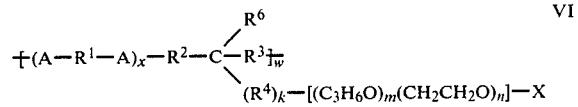

wherein A is

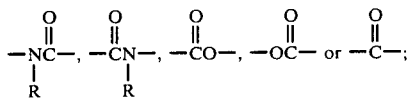

x is 0 or 1; R is H or $C_1$-$C_4$ alkyl or hydroxyalkyl; $R^1$ is $C_2$-$C_{12}$ alkylene, hydroxyalkylene, alkenylene, cycloalkylene, arylene or alkarylene, or a $C_2$-$C_3$ oxyalkylene moiety having from 2 to about 20 oxyalkylene units provided that no O—O or O—N bonds are formed with A; when x is 1, $R^2$ is —$R^4$— except when A is

or is —(OR⁷)ᵧ— or —OR⁴— provided that no O—O or N—O bonds are formed with A, and R³ is —R⁵— except that A is

or is —(R⁷O)—ᵧ or —R⁴O— provided that no O—O or O—N bonds are formed with A; when x is O, R² is —(OR⁷)ᵧ—, —OR⁴—,

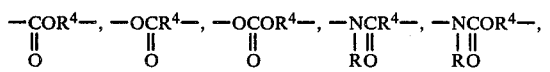

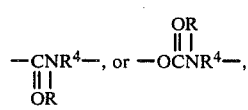

and R³ is —R⁴—; R⁴ is $C_1$-$C_{12}$ alkylene, hyroxyalkylene, alkenylene, arylene, or alkarylene; R⁵ is $C_1$-$C_4$ alkyl or hydroxyalkyl; R⁶ is H, $C_1$-$C_4$ alkyl or hydroxyalkyl, or the moiety —(R⁴)ₖ—[($C_3H_6O$)ₘ($CH_2CH_2O$)ₙ—]—X; R⁷ is $C_2$-$C_3$ alkylene or hydroxyalkylene; X is H,

—R⁸ or a mixture thereof, wherein R⁸ is $C_1$-$C_4$ alkyl or hydroxyalkyl; k is 0 or 1; m and n are numbers such that the moiety —($CH_2CH_2O$)ₙ— comprises at least about 85% by weight of the moiety —[($C_3H_6O$)ₘ($CH_2CH_2O$)ₙ]—; m is from 0 to about 5; n is at least about 3; y is from 2 to about 20; the number of u, v and w are such that there are at least 2

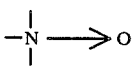

groups and at least 2 X groups.

In the above formulas IV, V and VI, A is preferably

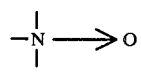

x is preferably 1; and R is preferably H. R¹ can be linear (e.g. —CH₂—CH₂—CH₂—,

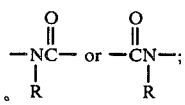

or branched (e.g.

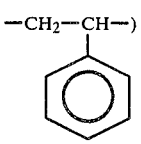

alkylene, hydroxyalkylene, alkenylene, cycloalkylene, alkarylene or oxyalkylene; when R¹ is a $C_2$-$C_3$ oxyalkylene moiety, the number of oxyalkylene units is preferably from 2 to about 12; R¹ is preferably $C_2$-$C_6$ alkylene or phenylene, and most preferably $C_2$-$C_6$ alkylene (e.g. ethylene, propylene, hexamethylene). R² is preferably —OR⁴— or —(OR⁷)ᵧ—; R³ is preferably —R⁴O— or —(R⁷O)ᵧ—; R⁵ is preferably methyl. Like R¹, R⁴ can be linear or branched, and is preferably $C_2$-$C_3$ alkylene; R⁶ is preferably H or $C_1$-$C_3$ alkyl; R⁷ is preferably ethylene; R⁸ is preferably methyl; X is preferably H or methyl; k is preferably 0; m is preferably 0; y is preferably from 2 to about 12.

In the above formulas IV, V and VI, n is preferably at least about 6 when the number of

groups and X groups is 2 or 3; n is most preferably at least about 12, with a typical range of from about 12 to about 42 for all ranges of u+v+w. For homopolymers (v and w are 0), u is preferably from about 3 to about 40, and is most preferably from about 3 to about 20. For random copolymers (u is preferably 0), v and w are each preferably from about 3 to about 40.

B. Polyacrylate, Polyacrylamide, Polyvinylether or Like Polymers

Another class of suitable amine oxide polymers are derived from polyacrylates, polyacrylamides, polyvinylethers and the like. These polymers comprise units selected from those having formulas VII, VIII and IX:

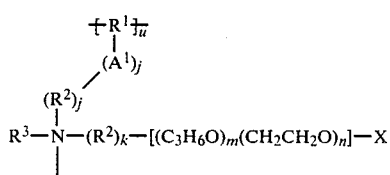

VII

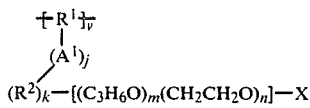

VIII

-continued $$+R^1+_w$$
$$(A^1)_j$$
$$(R^2)_j$$
$$N-(R^4)_2$$
$$\downarrow$$
$$O$$

IX wherein $A^1$ is $$-O-, -\overset{O}{\underset{R}{N}}\overset{\parallel}{C}-, -\overset{O}{\underset{R}{N}}\overset{\parallel}{C}O-, -\overset{O}{C}\overset{O}{\underset{R}{N}}\overset{\parallel}{C}-, -\overset{O}{C}\overset{\parallel}{\underset{R}{N}}-, -O\overset{O}{\underset{R}{C}}\overset{\parallel}{N}-$$

$$-O\overset{O}{\overset{\parallel}{C}}-, -O\overset{O}{\overset{\parallel}{C}}O-, -\overset{O}{\overset{\parallel}{C}}O-, \text{ or } -\overset{O}{\underset{R}{N}}\overset{\parallel}{C}\overset{O}{\underset{R}{N}}-;$$

R is H or $C_1$-$C_4$ alkyl or hydroxyalkyl; $R^1$ is substituted $C_2$-$C_{12}$ alkylene, hydroxyalkylene, alkenylene, arylene or alkarylene, or $C_2$-$C_3$ oxyalkylene; each $R^2$ is $C_1$-$C_{12}$ alkylene, hydroxyalkylene, alkenylene, arylene or alkarylene; each $R^3$ is $C_1$-$C_4$ alkyl or hyroxyalkyl, or the moiety $-(R^2)_k-[(C_3H_6O)_m(CH_2CH_2O)_n]-X$; each $R^4$ is $C_1$-$C_4$ alkyl or hydroxyalkyl, or two $R^4$ together form the moiety $-(CH_2)_r-A^2-(CH_2)_s-$, wherein $A^2$ is $-O-$ or $-CH_2-$; X is H, $$-\overset{O}{\overset{\parallel}{C}}R^5,$$

$-R^5$ or a mixture thereof, wherein $R^5$ is $C_1$-$C_4$ alkyl or hydroxyalkyl; j is 1 or 0; k is 1 or 0; m and n are numbers such that the moiety $-(CH_2CH_2O)_n-$ comprises at least about 85% by weight of the moiety $-[(C_3H_6O)_m(CH_2CH_2O)_n]-$; m is from 0 to about 5; n is at least about 3; r is 1 or 2, s is 1 or 2 and r+s is 3 or 4; the number of u, v and w are such that there are at least 2

$$-\overset{|}{\underset{|}{N}}\longrightarrow O$$

groups and at least 2 X groups.

In the above formulas VII, VIII and IX, $A^1$ is preferably $$-\overset{O}{\overset{\parallel}{C}}\overset{}{\underset{R}{N}}-, -\overset{O}{\overset{\parallel}{C}}O- \text{ or } -O-;$$

$A^2$ is preferably $-O-$; R is preferably H. $R^1$ can be linear (e.g.

$-CH_2-CH-CH_2-, -CH_2CH-$ )
         |              |
         (phenyl)   (phenyl)

IX or branched (e.g.

$-CH_2-\underset{\underset{CH_3}{|}}{\overset{\overset{CH_3}{|}}{C}}-, -CH_2CH-, -CH_2\underset{\underset{CH_2}{|}}{\overset{\overset{CH_3}{|}}{C}}-, -CH_2\underset{\underset{CH_2}{|}}{\overset{\overset{phenyl}{|}}{C}}-$ )

substituted alkylene, hydroxyalkylene, alkenylene, alkarylene or oxyalkylene; $R^1$ is preferably substituted $C_2$-$C_6$ alkylene or substituted $C_2$-$C_3$ oxyalkylene, and most preferably $$-CH_2CH- \text{ or } -CH_2-\overset{\overset{CH_3}{|}}{\underset{|}{C}}-.$$

Each $R^2$ is preferably $C_2$-$C_3$ alkylene; $R^3$ and each $R^4$ are preferably methyl; $R^5$ is preferably methyl; X is preferably H or methyl; j is preferably 1; k is preferably 0; m is preferably 0; r and s are each preferably 2.

In the above formulas VII, VIII and IX, n, u, v and w can be varied according to the n, u, v and w for the preceding polyurethane and like polymers (formulas IV, V and VI).

C. Polyalkyleneamine, Polyalkyleneimine or Like Polymers

Another class of suitable amine oxide polymers are derived from polyalkyleneamines, polyalkyleneimines and the like. These polymers comprise units selected from those having formulas X, XI and XII:

$$+R^1-M^4+_x \qquad +R^1-\overset{|}{\underset{(R^2)_k-[(C_3H_6O)_m(CH_2CH_2O)_n]-X}{M^4}}+_y$$

X                                 XI $$+R^1-\overset{\overset{R^3}{|}}{\underset{(R^2)_k-[(C_3H_6O)_m(CH_2CH_2O)_n]-X}{M^4}}]_z$$

XII wherein $R^1$ is $C_2$-$C_{12}$ alkylene, hydroxyalkylene, alkenylene, cycloalkylene, arylene or alkarylene, or a $C_2$-$C_3$ oxyalkylene moiety having from 2 to about 20 oxyalkylene units provided that no O-N bonds are formed; $R^2$ is $C_1$-$C_{12}$ alkylene, hydroxyalkylene, alkenylene, arylene or alkarylene; $R^3$ is $C_1$-$C_4$ alkyl or hydroxyalkyl, or the moiety —$(R^2)_k$ —$[(C_3H_6O)_m(CH_2CH_2O)_n]$—X; $M^4$ is an

group; X is H,

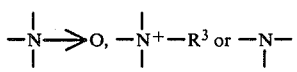

—$R^4$ or a mixture thereof,
wherein $R^5$ is $C_1$–$C_4$ alkyl of hydroxyalkyl; k is 1 or 0; m and n are numbers such that the moiety —$(CH_2CH_2O)_n$— comprises at least about 85% by weight of the moiety —$[(C_3H_6O)_m(CH_2CH_2O)]_n$—; m is from 0 to about 5; n is at least about 3; the number of x, y and z are such that there are at least 2 $M^4$ groups, at least 2

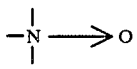

groups and at least 2 X groups.

In the above formulas X, XI and XII, $R^1$ can be varied like $R^1$ of the preceding polyurethane and like polymers (formulas IV, V and VI); $R^2$ is preferably $C_2$–$C_3$ alkylene; $R^3$ is preferably methyl or the moiety —$(R^2)_k$—$[(C_3H_6O)_m (CH_2CH_2O)_n]$—X; $R^4$ is preferably methyl; X is preferably H; k is preferably 0; m is preferably 0.

In the above formulas X, XI and XII, n is preferably at least about 6 when the number of $M^4$ and X groups is 2 or 3; n is most preferably at least about 12, with a typical range of from about 12 to about 42 for all ranges of x+y+z. Typically, x+y+z is from 2 to about 40, and preferably from 2 to about 20. For short chain length polymers, x+y+z can range from 2 to 9 with from 2 to 9

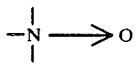

groups and from 2 to 11 X groups. For long chain length polymers, x+y+z is at least 10, with a preferred range of from 10 to about 42. For the short and long chain length polymers, the $M^4$ groups can be a mixture of from about 30 to 100%

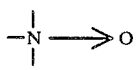

groups, and from 0 to about 70%

groups,

groups or mixtures thereof. Preferably, the $M^4$ groups comprise a mixture of from about 70 to 100%

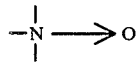

groups, and from 0 to about 30%

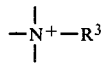

groups,

groups or mixtures thereof.

Preferred amine oxide polymers within this class are derived from the $C_2$–$C_3$ polyalkyleneamines (x+y+z is from 2 to 9) and polyalkyleneimines (x+y+z is at least 10, preferably from 10 to about 42). Particularly preferred polyalkyleneamine oxides and polyalkyleneimine oxides are the polyethyleneamine (PEA) oxides and polyethyleneimine (PEI) oxides. These preferred amine oxide polymers have the following general formula XIII:

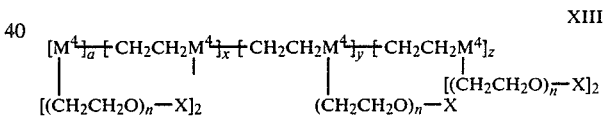

wherein $M^4$, X, x, y, z and n are defined as before, and a is 1 or 0. Within the above formula XIII, the various units can be mixed and arranged to provide linear, branched or cyclic amine oxide polymers.

Prior to ethoxylation, the PEAs used in preparing amine oxide polymers of the present invention have the following general formula XIV:

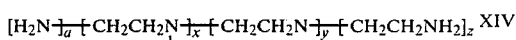

wherein x+y+z is from 2 to 9, and a is 0 or 1 (molecular weight of from about 100 to about 400). Each hydrogen atom attached to each nitrogen atom represents an active site for subsequent ethoxylation. For preferred PEAs, x+y+z is from about 3 to about 7 (molecular weight of from about 140 to about 310) These PEAs can be obtained by reactions involving ammonia and ethylene dichloride, followed by fractional distillation. The common PEAs obtained are triethylenetetramine (TETA) and tetraethylenepentamine (TEPA). Above the pentamines, i.e., the hexamines, heptamines, octamines and possibly nonamines the cogenerically derived mixture does not appear to separate by distillation and can include other materials such as cyclic amines and particularly piperazines; these cyclic amines can also be present in mixtures containing TETA and TEPA. There can also be present cyclic amines with side chains in which nitrogen atoms appear. See U.S. Pat. No. 2,792,372 to Dickson, issued May 14, 1957, which describes the preparation of PEAs.

The minimum degree of ethoxylation required for preferred clay soil removal/anti-redeposition performance can vary depending upon the number of units in the PEA. Where y+z is 2 or 3, n is preferably at least about 6. Where y+z is from 4 to 9, suitable benefits are achieved when is at least about 3. For preferred PEA oxides, n is at least about 12, with a typical range of from about 12 to about 42.

The PEIs used in preparing the amine oxide polymers of the present invention have a molecular weight of at least about 440 prior to ethoxylation, which represents at least about 10 units. Preferred PEIs used in preparing these polymers have a molecular weight of from about 600 to about 1800. The polymer backbone of these PEIs can be represented by the general formula XV:

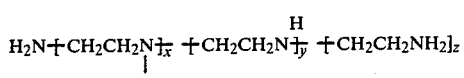

XV wherein the sum of x, y and z represents a number of sufficient magnitude to yield a polymer having the molecular weights previously specified. Although linear polymer backbones are possible, branch chains can also occur. The relative proportions of primary, secondary and tertiary amine groups present in the polymer can vary, depending on the manner of preparation. The distribution of amine groups is typically as follows:

| | |
|---|---|
| $-CH_2CH_2-NH_2$: | 30% |
| $-CH_2CH_2-NH-$: | 40% |
| $-CH_2CH_2-N-$ | 30% |

Each hydrogen atom attached to each nitrogen atom of the PEI represents an active site for subsequent ethoxylation. These PEIs can be prepared, for example, by polymerizing ethyleneimine in the presence of a catalyst such as carbon dioxide, sodium bisulfite, sulfuric acid, hydrogen peroxide, hydrochloric acid, acetic acid, etc. Specific methods for preparing PEIs are disclosed in U.S. Pat. No. 2,182,306 to Ulrich et al., issued Dec. 5, 1939; U.S. Pat. No. 3,033,746 to Mayle et al., issued May 8, 1962; U.S. Pat. No. 2,208,095 to Esselmann et al., issued July 16, 1940; U.S. Pat. No. 2,806,839 to Crowther, issued Sept. 17, 1957; and U.S. Pat. No. 2,553,696 to Wilson, issued May 21, 1951 (all herein incorporated by reference).

As defined in the preceding formulas, n is at least about 3 for the PEI oxides. However, it should be noted that the minimum degree of ethoxylation required for suitable clay soil removal/anti-redeposition performance can increase as the molecular weight of the PEI increases, especially much beyond about 1800. Also, the degree of ethoxylation for preferred polymers increases as the molecular weight of the PEI increases. For PEIs having a molecular weight of at least about 600, n is preferably at least about 12, with a typical range of from about 12 to about 42. For PEIs having a molecular weight of at least 1800, n is preferably at least about 24, with a typical range of from about 24 to about 42.

D. Diallylamine Polymers

Another class of suitable amine oxide polymers are those derived from the diallylamines. These polymers comprise units selected from those having formulas XVI and XVII:

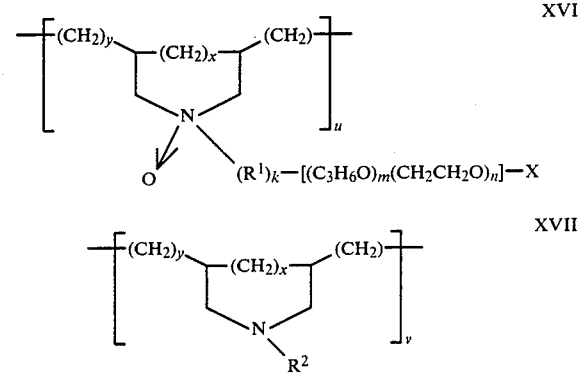

wherein $R^1$ is $C_1-C_{12}$ alkylene, hydroxylalkylene, alkylene, arylene or alkarylene; $R^2$ is $C_1-C_4$ alkyl or hydroxyalkyl; X is H,

$-R^3$ or a mixture thereof, wherein $R^3$ is $C_1-C_4$ alkyl or hydroxyalkyl; k is 1 or 0; m and n are numbers such that the moiety $-(CH_2CH_2O)_n-$ comprises at least about 85% by weight of the moiety $[(C_3H_6O)_m(CH_2CH_2O)_n]-$; m is from 0 to about 5; n is at least about 3; x is 1 or 0; y is 1 when x is 0, and O when x is 1; the number of u and v are such that there are at least 2

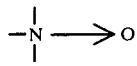

groups and at least 2 X groups.

In the above formulas XVI and XVII, $R^1$ is preferably $C_2-C_3$ alkylene; $R^2$ is preferably methyl; $R^3$ is preferably methyl; X is preferably H; k is preferably O; m is preferably O.

In the above formulas XVI and XVII, n is preferably at least about 6 when the numbr of

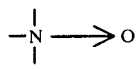

groups and X groups are each 2 or 3, n is preferably at least 12, with a typical range of from about 12 to about 42 for all ranges of u+v. Typically, v is 0, and u is from 2 to about 40, and preferably from 2 to about 20.

Methods for Making Amine Oxide Polymers

A. Polyurethane

The polyurethane versions of the present invention can be prepared according to the following general scheme.

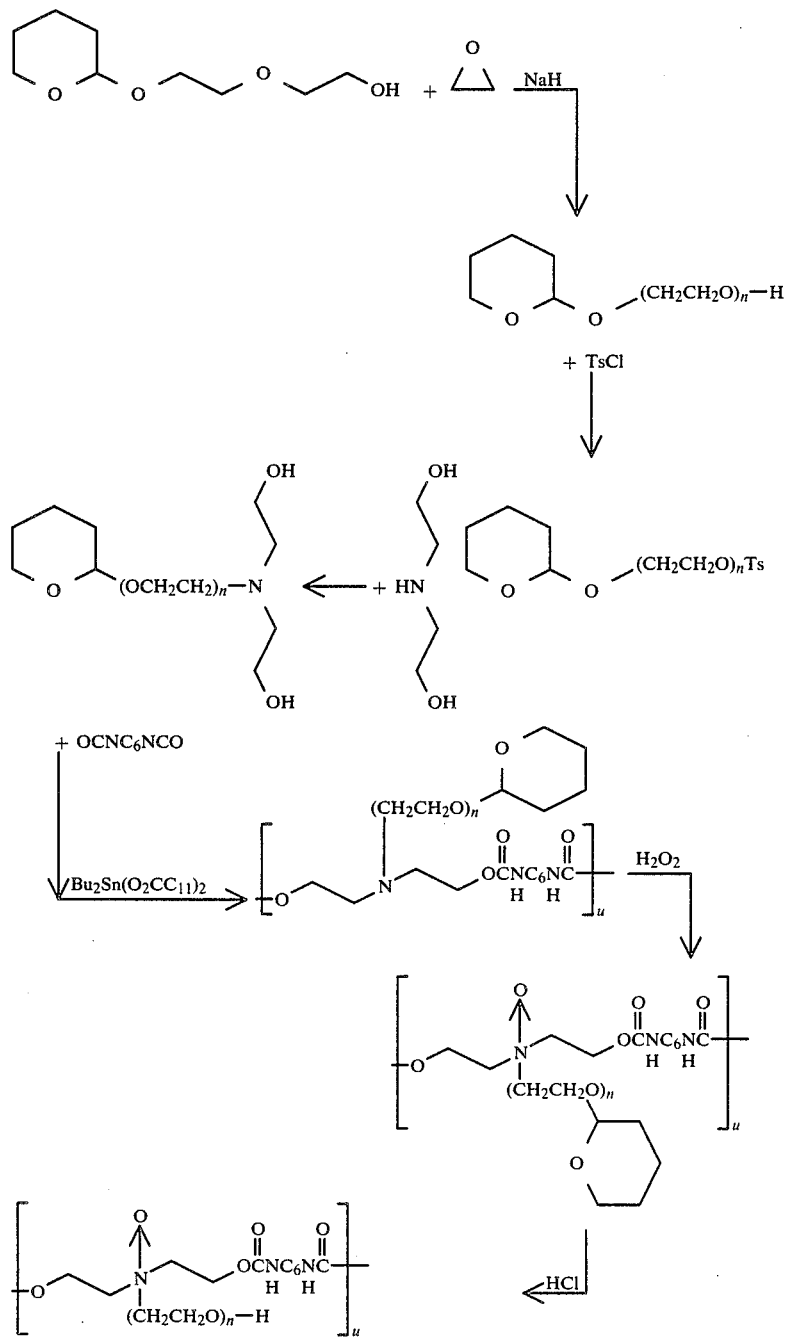

The synthesis of one such polyurethane is described as follows:

EXAMPLE 3

Step 1: Ethoxylation

The monotetrahydropyranyl ether of diethylene glycol (B 1.77 moles) [Compt. Rend., 260, 1399-1401 (1965)] is ethoxylated using 5 mole % NaH to generate a catalytic amount of the corresponding alkoxide. Ethoxylation is conducted at 90°-120° C. until about 22 moles (n=22) of ethylene oxide is taken up for each mole of the starting alcohol to form the ethoxylated compound.

Step 2: Tosylation

The ethoxylated compound from step 1 is dissolved in 1000 ml. of acetonitrile and then cooled to about 10° C. To this solution is added 2.7 moles of tosyl chloride dissolved in 500 ml. of acetonitrile and cooled to 10° C. and then 2.9 moles of triethylamine is added. After the reaction is complete, H$_2$O is added to decompose the remaining tosyl chloride.

Step 3: Amination

To the reaction mixture from step 3 is added 3.4 moles of diethanolamine. After heating for 18 hrs. at 80° C., the reaction mixture is cooled and carefully acidified with HCl to a pH just above 7 and then extracted with ether. The aqueous phase is then extracted with a mixture of ether:acetonitrile (ratio of about 5:2) twice. The aqueous phase is separated and then made basic with 50% NaOH. This aqueous phase is extracted with dichloromethane (2000 ml.). The lower layer is separated and then extracted 3 times with 2000 ml. portions of ¼ saturated NaCl solution while adding enough 50% NaOH solution to make the aqueous phase strongly basic (pH of about 11). The lower organic layer is stripped to give the desired aminated compound. Toluene (200 ml.) is added and the mixture is stripped again to give the desired aminated monomer.

Step 4: Polymerization

The monomer from step 3 is dissolved in chloroform free of ethanol stabilizer. The monomer is previously evacuated in a Kugelrohr at 80°–90° C. under a vacuum (pressure of 1 mm.) for at least 18 hours. The monomer in the chloroform is then dried overnight with 3 Å molecular sieves and then transferred to a dry flask (equipped with mechanical stirrer) under argon. To the monomer is added dibutyltin dilaurate catalyst (0.058 mole equiv.) in chloroform under argon. To the stirred reaction mixture is then added 0.7 moles of hexamethylenediisocyanate per mole of aminated monomer over a 5 minute period. The reaction mixture is stirred at room temperature for 18 hours. The chloroform is removed under a vacuum at about 70° C. to give the resulting polymer.

Step 5: Oxidation and Removal of Protecting Groups

The polymer from step 5 (0.01 equivalents of titratable amino groups) and distilled water (50 ml.) are placed in a flask. The solution is then adjusted to pH 10. A 30% H₂O₂ solution (0.1 mole equiv.) is added and the reaction mixture is then stirred at 65° C. for 2 hours. A dozen ⅛″ alumina pellets impregnated with 0.5% platinum are added to the mixture which is permitted to stand at 65° C. with occasional stirring until a very low peroxide titration is obtained. The pH of the mixture is then adjusted to about 4 with aqueous HCl and is allowed to stand overnight to solvolyze the tetrahydropyranyl protecting group. The solution is then neutralized with NaOH and stripped to give the crude polyurethane containing amine oxide groups. This crude polyurethane is dissolved in chloroform and filtered to remove any salts. The chloroform is stripped away to give the desired, largely salt-free amine oxide polymer.

B. Random Copolymer of Ethoxylated Acrylate and an Amine Oxide of Methacrylamide The random copolymer versions of the present invention can be prepared according to the following general scheme:

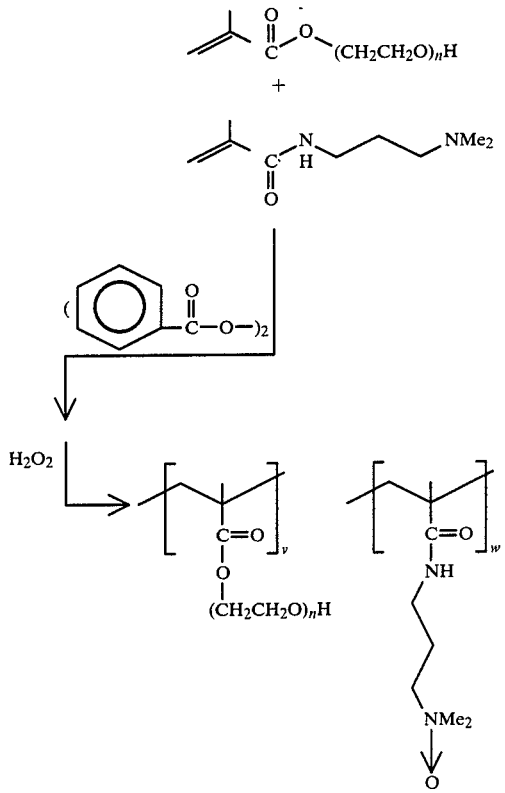

The synthesis of one such random copolymer is described as follows:

EXAMPLE 4

Decaethylene glycol monomethacrylate monomer (0.008 moles) and N-(3-dimethylaminopropyl)-methacrylamide monomer (0.011 moles) are dissolved in 40 ml. of acetonitrile. The reaction mixture is purged of oxygen by bubbling argon through it. A 0.23 g. portion of benzoyl peroxide is separately dissolved in 10 ml. of acetonitrile and similarly purged. The reaction mixture is heated to reflux and the benzoyl peroxide solution then added dropwise over 0.5 hours. Next, 0.28 g. of azobisisobutyronitrile in 5 ml. of acetonitrile is added to the reaction mixture and heating is continued overnight. The polymer obtained (0.01 equivalents of titratable amino groups) is placed with distilled water (50 ml.) in a flask. The solution pH is then maintained at pH 9. A 30% H₂O₂ solution (0.1 mole equiv.) is added and the reaction mixture is then stirred at 65° C. for 2 hours. A dozen ⅛″ alumina pellets impregnated with 0.5% platinum are then added to the mixture which is permitted to stand at 65° C. with occasional stirring until a very low peroxide titration is obtained. The amine oxide polymer is then obtained by stripping the solvent at 50° C. under a vacuum.

C. Polyethyleneamine and Polyethyleneimine Oxides

The polyethyleneamine and polyethyleneimine oxides can be prepared using standard methods for ethoxylating amines, with subsequent oxidation by H₂O₂. Representatiave syntheses of each polyethyleneamine and polyethyleneimine oxides are as follows:

EXAMPLE 5a

Step 1: Ethoxylation

Tetraethylenepentamine (TEPA) (M.W. 189, 94.5 g., 0.51 moles) was placed in a nominally dry flask and dried by stirring for 0.5 hrs. at 110°-120° C. under vacuum (pressure less than 1 mm Hg.). The vacuum was released by drawing ethylene oxide (EO) from a pre-purged trap connected to a supply tank. Once the flask was filled with EO, an outlet stopcock was carefully opened to a trap connected to an exhaust bubbler. After 10 hrs. stirring at 100°-110° C., a total of 1601 g. EO was taken up to give a degree of ethoxylation of 1.04 per reactive site. In a similar apparatus, the hydroxyethylated TEPA (202.8 g., 0.41 moles) was mixed with a 40% KOH solution (10.1 g.) and stirred under a vacuum for 1 hr. at 110° C. to remove all water. The stirred reaction mixture was then swept with argon. EO was then added to the mixture as a sweep under atmospheric pressure at 110°-120° C. with moderately fast stirring. After 13 hrs., 1775 g. (40.3 moles) of EO had been added to give a calculated total degree of ethoxylation of 15.1.

Step 2: Oxidation

The ethoxylated TEPA from step 1 (103.1 g., 0.021 moles) and distilled water (240 ml.) were added together and the solution was adjusted to pH 10 with 1N HCl. A 33.5% $H_2O_2$ solution (0.117 mole equiv.) was added and the reaction mixture was then heated by a 65°-70° C. temperature water bath for 6.5 hrs. During this period, the pH of the mixture slowly dropped from 10 to about 8.5 several times; each time the pH reached 8.5, it was adjusted back to 10 with dilute NaOH solution. A dozen ⅛" alumina pellets impregnated with 0.5% platinum were added to the mixture to destroy residual $H_2O_2$; the mixture was also heated at 65°-70° C. for 10 hrs. to aid in this destruction. The pellets were then removed and the mixture concentrated on a rotary evaporator to 80% amine oxide polymer assuming a yield of 104.4 g. (0.021 moles). Analysis indicated that 88.2% of the tertiary amine groups had been oxidized.

EXAMPLE 5b

Step 1: Ethoxylation

By a procedure similar to that of Example 5a, PEI (21.5 g., M.W. 600, 0.4 moles) was dried at 120° C. under vacuum and swept with EO until hydroxyethylation was nearly complete (5 hrs.). The hydroxyethylated PEI was cooled under argon and 1.0 g. (0.025 moles) of 60% NaH in mineral oil was then added. The reaction mixture was heated to about 140° C. and was swept for 32 hrs. with EO until a total of 603.5 g. of EO was added which gave a calculated degree of ethoxylation of 23.2.

Step 2: Oxidation

The 23.2 ethoxylated PEI from Step 1 (15 g., 0.00087 moles) and distilled water (15 ml.) were added together and the solution adjusted to pH 8.3 with 1N HCl. A 30% $H_2O_2$ solution (0.015 mole equiv.) was added and the reaction mixture was then heated in a 65°-70° C. temperature water bath for 15 hrs. The pH of the mixture was adjusted when necessary to maintain the pH within the range of 8.5-10. A dozen ⅛" alumina pellets impregnated with 0.5% platinum were added to the reaction mixture which was allowed to stand at room temperature until oxygen evolution ceased. The pellets were then removed and the mixture was concentrated to 80% amine oxide polymer. Analysis indicated that 67.7% of the tertiary amine groups had been oxidized.

D. Diallylamine Polymers

Diallylamine polymer versions of the present invention can be prepared according to the following general scheme:

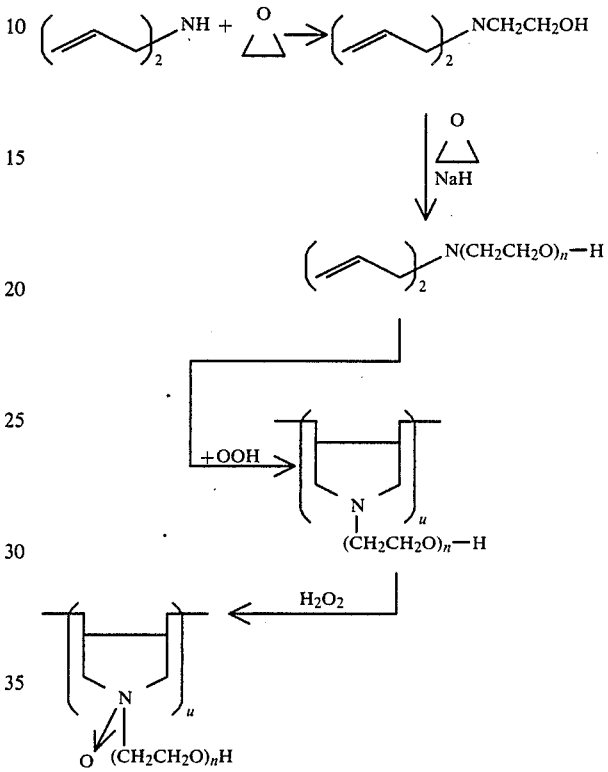

The synthesis of one such polymer is described as follows:

EXAMPLE 6

Step 1: Ethoxylation

Diallylaine (1.7 moles) is dissolved in methanol (160 ml.) under argon and then heated to 45° C. Ethylene oxide is then added for 2.5 hours. Methanol is then removed by heating the reaction mixture to 100° C. in vacuo. To the residue is added sodium hydride in mineral oil (6.6 g., 0.17 moles) with stirring until the evolution of hydrogen has ceased. Ethylene oxide is then added until the degree of ethoxylation (n) is about 7.

Step 2: Polymerization

The ethoxylated diallylamine monomer from step 1 (20 g) is mixed with $D_2O$ (20 ml.) and is heated to 95° C. under argon for 1 hour. Tertbutylhydroperoxide (25 drops) is then added and the reaction continued at 90° C. for 18 hours. Then 20 more drops of the hydroperoxide is added. After heating 3 more days, water is then removed in vacuo (50°-60° C. at pressure of 0.1 mm) to yield the crude polymer.

Step 3: Oxidation

The crude diallylamine polymer from step 2 (15 g., 0.04 equivalents of titratable amino groups) and distilled water (50 ml.) are added together and the solution adjusted to pH 10 with 1N NaOH. A 30% $H_2O_2$ solution (0.06 mole equiv.) is added and the reaction mixture is then heated by a 65°-70° C. temperature water bath for 18 hrs. The pH of the mixture is adjusted when necessary to maintain the pH within the range of 8.5-10. A dozen ⅛" alumina pellets impregnated with 0.5% platinum are added to the reaction mixture to destroy residual $H_2O_2$. The pellets are then removed and the mixture is concentrated to 80% amine oxide polymer.

Detergent Compositions

The level at which the amine oxides can be present in the detergent compositions of the present invention can vary depending upon the compounds used, the particular detergent formulation (liquid, granular) and the benefits desired. These compositions can be used as laundry detergents, laundry additives, and laundry pretreatments. Although the detergent compositions of the present invention are normally used as is, they can also be impregnated into a suitable substrate for use. Generally, the compounds can be included in an amount of from about 0.05 to about 95% by weight of the composition, with the usual range being from 0.1 to about 10% by weight for laundry detergents. In terms of the benefits achieved, preferred detergent compositions can comprise from about 0.5 to about 5% by weight of the compounds of the present invention. Typically, these preferred compositions comprise from about 1 to about 3% by weight of these compounds. These compounds are normally present at a level that provides from about 2 ppm to about 200 ppm, preferably from about 10 ppm to about 100 ppm, of the compound in the wash solution at recommended U.S. usage levels, and normally from about 30 ppm to about 1000 ppm, preferably from about 50 ppm to about 500 ppm for European usage levels.

Detergent Surfactants

The amount of detergent surfactant included in the detergent compositions of the present invention can vary from about 1 to about 75% by weight of the composition depending upon the detergent surfactant(s) used, the type of composition to be formulated (e.g. granular, liquid) and the effects desired. Preferably, the detergent surfactant(s) comprises from about 10 to about 50% by weight of the composition. The detergent surfactant can be nonionic, anionic, ampholytic, zwitterionic, cationic, or a mixture thereof:

A. Nonionic Surfactants

Suitable nonionic surfactants for use in detergent compositions of the present invention are generally disclosed in U.S. Pat. No. 3,929,678 to Laughlin et al., issued Dec. 30, 1975 at column 13, line 14 through column 16, line 6 (herein incorporated by reference). Classes of nonionic surfactants included are:

1. The polyethyleneoxide condensates of alkyl phenols. These compounds include the condensation products of alkyl phenols having an alkyl group containing from about 6 to 12 carbon atoms in either a straight chain or branched chain configuration with ethylene oxide, the ethylene oxide being present in an amount equal to 5 to 25 moles of ethylene oxide per mole of alkyl phenol. The alkyl substituent in such compounds can be derived, for example, from polymerized propylene, diisobutylene, and the like. Examples of compounds of this type include nonyl phenol condensed with about 9.5 moles of ethylene oxide per mole of nonyl phenol; dodecylphenol condensed with about 12 moles of ethylene oxide per mole of phenol; dinonyl phenol condensed with about 15 moles of ethylene oxide per mole of phenol; and diisooctyl phenol condensed with about 15 moles of ethylene oxide per mole of phenol. Commercially available nonionic surfactants of this type include Igepal CO-630, marketed by the GAF Corporation, and Triton X-45, X-114, X-100, and X-102, all marketed by the Rohm & Haas Company.

2. The condensation products of aliphatic alcohols with from about 1 to about 25 moles of ethylene oxide. The alkyl chain of the aliphatic alcohol can either be straight or branched, primary or secondary, and generally contains from about 8 to about 22 carbon atoms. Examples of such ethoxylated alcohols include the condensation product of myristyl alcohol condensed with about 10 moles of ethylene oxide per mole of alcohol; and the condensation product of about 9 moles of ethylene oxide with coconut alcohol (a mixture of fatty alcohols with alkyl chains varying in length from 10 to 14 carbon atoms). Examples of commercially available nonionic surfactants of this type include Tergitol 15-S-9, marketed by Union Carbide Corporation, Neodol 45-9, Neodol 23-6.5, Neodol 45-7, and Neodol 45-4, marketed by Shell Chemical Company, and Kyro EOB, marketed by The Procter & Gamble Company.

3. The condensation products of ethylene oxide with a hydrophobic base formed by the condensation of propylene oxide with propylene glycol. The hydrophobic portion of these compounds has a molecular weight of from about 1500 to 1800 and exhibits water insolubility. The addition of polyoxyethylene moieties to this hydrophobic portion tends to increase the water solubility of the molecule as a whole, and the liquid character of the product is retained up to the point where the polyoxyethylene content is about 50% of the total weight of the condensation product, which corresponds to condensation with up to about 40 moles of ethylene oxide. Examples of compounds of this type include certain of the commercially available Pluronic surfactants, marketed by Wyandotte Chemical Corporation.

4. The condensation products of ethylene oxide with the product resulting from the reaction of propylene oxide and ethylenediamine. The hydrophobic moiety of these products consists of the reaction product of ethylenediamine and excess propylene oxide, the moiety having a molecular weight of from about 2500 to about 3000. This hydrophobic moiety is condensed with ethylene oxide to the extent that the condensation product contains from about 40% to about 80% by weight of polyoxyethylene and has a molecular weight of from about 5,000 to about 11,000. Examples of this type of nonionic surfactant include certain of the commercially available Tetronic compounds, marketed by Wyandotte Chemical Corporation.

5. Semi-polar nonionic detergent surfactants which include water-soluble amine oxides containing one alkyl moiety of from about 10 to 18 carbon atoms and 2 moieties selected from the group consisting of alkyl groups and hydroxyalkyl groups containing from 1 to about 3 carbon atoms; water-soluble phosphine oxides containing one alkyl moiety of from about 10 to 18 carbon atoms and 2 moieties selected from the group consisting of alkyl groups and hydroxyalkyl groups containing from about 1 to 3 carbon atoms; and water-soluble sulfoxides containing one alkyl moiety of from about 10 to 18 carbon atoms and a moiety selected from the group consisting of alkyl and hydroxyalkyl moieties of from about 1 to 3 carbon atoms.

Preferred semi-polar nonionic detergent surfactants are the amine oxide detergent surfactants having the formula

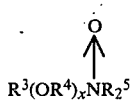

wherein $R^3$ is an alkyl, hydroxyalkyl, or alkyl phenyl group or mixtures thereof containing from about 8 to about 22 carbon atoms; $R^4$ is an alkylene or hydroxyalkylene group containing from 2 to 3 carbon atoms or mixtures thereof; x is from 0 to about 3; and each $R^5$ is an alkyl or hydroxyalkyl group containing from 1 to about 3 carbon atoms or a polyethylene oxide group containing from one to about 3 ethylene oxide groups. The $R^5$ groups can be attached to each other, e.g., through an oxygen or nitrogen atom to form a ring structure.

Preferred amine oxide detergent surfactants are $C_{10}$–$C_{18}$ alkyl dimethyl amine oxide and $C_8$–$C_{12}$ alkoxy ethyl dihydroxy ethyl amine oxide.

6. Alkylpolysaccharides disclosed in U.S. application Ser. No. 371,747 to Ramon A. Llenado, filed Apr. 26, 1982, having a hydrophobic group containing from about 6 to about 30 carbon atoms, preferably from about 10 to about 16 carbon atoms and a polysaccharide, e.g., a polyglycoside, hydrophilic group containing from about 1½ to about 10, preferably from about 1½ to about 3, most preferably from about 1.6 to about 2.7 saccharide units. Any reducing saccharide containing 5 or 6 carbon atoms can be used, e.g. glucose, galactose and galactosyl moieties can be substituted for the glucosyl moieties. (Optionally the hydrophobic group is attached at the 2, 3, 4, etc. positions thus giving a glucose or galactose as opposed to a glucoside or galactoside.) The intersaccharide bonds can be, e.g., between the one position of the additional saccharide units and the 2-, 3-, 4-, and/or 6 positions on the preceding saccharide units.

Optionally, and less desirably, there can be a polyalkyleneoxide chain joining the hydrophobic moiety and the polysaccharide moiety. The preferred alkyleneoxide is ethylene oxide. Typical hydrophobic groups include alkyl groups, either saturated or unsaturated, branched or unbranched containing from about 8 to about 18, preferably from about 10 to about 16, carbon atoms. Preferably, the alkyl group is a straight chain saturated alkyl group. The alkyl group can contain up to 3 hydroxy groups and/or the polyalkyleneoxide chain can contain up to about 10, preferably less than 5, most preferably 0, alkyleneoxide moieties. Suitable alkyl polysaccharides are octyl, nonyldecyl, undecyldodecyl, tridecyl, tetradecyl, pentadecyl, hexadecyl, heptadecyl, and octadecyl, di-, tri-, tetra-, penta-, and hexaglucosides, galactosides, lactosides, glucoses, fructosides, fructoses, and/or galactoses. Suitable mixtures include coconut alkyl, di-, tri-, tetra-, and pentaglucosides and tallow alkyl tetra-, penta-, and hexaglucosides.

The preferred alkylpolyglycosides have the formula

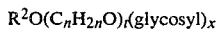

wherein $R^2$ is selected from the group consisting of alkyl, alkylphenyl, hydroxyalkyl, hydroxyalkylphenyl, and mixtures thereof in which the alkyl groups contain from about 10 to about 18, preferably from about 12 to about 14, carbon atoms; n is 2 or 3, preferably 2; t is from 0 to about 10, preferably 0; and x is from 1½ to about 10, preferably from about 1½ to about 3, most preferably from about 1.6 to about 2.7. The glycosyl is preferably derived from glucose. To prepare these compounds, the alcohol or alkylpolyethoxy alcohol is formed first and then reacted with glucose, or a source of glucose, to form the glucoside (attachment at the 1-position). The additional glycosyl units can then be attached between their 1-position and the preceding glycosyl units 2-, 3-, 4- and/or 6-position, preferably predominately the 2-position.

7. Fatty acid amide detergent surfactants having the formula:

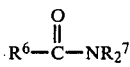

wherein $R^6$ is an alkyl group containing from about 7 to about 21 preferably from about 9 to about 17) carbon atoms and each $R^7$ is selected from the group consisting of hydrogen, $C_1$–$C_4$ alkyl, $C_1$–$C_4$ hydroxyalkyl, and —$(C_2H_4O)_xH$ where x varies from about 1 to about 3.

Preferred amides are $C_8$–$C_{20}$ ammonia amides, monoethanolamides, diethanolamines, and isopropanol amides.

B. Anionic Surfactants

Anionic surfactants suitable in detergent compositions of the present invention are generally disclosed in U.S. Pat. No. 3,929,678 to Laughlin et al., issued Dec. 30, 1975 at column 23, line 58 through column 29, line 23 (herein incorporated by reference). Classes of anionic surfactants included are:

1. Ordinary alkali metal soaps such as the sodium, potassium, ammonium and alkylolammonium salts of higher fatty acids containing from about 8 to about 24 carbon atoms, preferably from about 10 to about 20 carbon atoms.

2. Water-soluble salts, preferably the alkali metal, ammonium and alkylolammonium salts, of organic sulfuric reaction products having in their molecular structure an alkyl group containing from about 10 to about 20 carbon atoms and a sulfonic acid or sulfuric acid ester group. (Included in the term "alkyl" is the alkyl portion of acyl groups.)

Examples of this group of anionic surfactants are the sodium and potassium alkyl sulfates, especially those obtained by sulfating the higher alcohols ($C_8$–$C_{18}$ carbon atoms) such as those produced by reducing the glycerides of tallow or coconut oil; and the sodium and potassium alkylbenzene sulfonates in which the alkyl group contains from about 9 to about 15 carbon atoms, in straight chain or branched chain configuration, e.g., those of the type described in U.S. Pat. Nos. 2,220,099 and 2,477,383. Especially valuable are linear straight chain alkylbenzene sulfonates in which the average number of carbon atoms in the alkyl group is from about 11 to 13, abbreviated as $C_{11}$–$C_{13}$LAS.

Preferred anionic surfactants of this type are the alkyl polyethoxylate sulfates, particularly those in which the alkyl group contains from about 10 to about 22, preferably from about 12 to about 18 carbon atoms, and wherein the polyethoxylate chain contains from about 1 to about 15 ethoxylate moieties preferably from about 1 to about 3 ethoxylate moieties. These anionic detergent surfactants are particularly desirable for formulating heavy-duty liquid laundry detergent compositions.

Other anionic surfactants of this type include sodium alkyl glyceryl ether sulfonates, especially those ethers of higher alcohols derived from tallow and coconut oil;

sodium coconut oil fatty acid monoglyceride sulfonates and sulfates; sodium or potassium salts of alkyl phenol ethylene oxide ether sulfates containing from about 1 to about 10 units of ethylene oxide per molecule and wherein the alkyl groups contain from about 8 to about 12 carbon atoms; and sodium or potassium salts of alkyl ethylene oxide ether sulfates containing about 1 to about 10 units of ethylene oxide per molecule and wherein the alkyl group contains from about 10 to about 20 carbon atoms.

Also included are water-soluble salts of esters of alphasulfonated fatty acids containing from about 6 to 20 carbon atoms in the fatty acid group and from about 1 to 10 carbon atoms in the ester group; water-soluble salts of 2-acyloxy-alkane-1-sulfonic acids containing from about 2 to 9 carbon atoms in the acyl group and from about 9 to about 23 carbon atoms in the alkane moiety; alkyl ether sulfates containing from about 10 to 20 carbon atoms in the alkyl group and from about 1 to 30 moles of ethylene oxide; water-soluble salts of olefin sulfonates containing from about 12 to 24 carbon atoms; and beta-alkyloxy alkane sulfonates containing from about 1 to 3 carbon atoms in the alkyl group and from about 8 to 20 carbon atoms in the alkane moiety.

3. Anionic phosphate surfactants.
4. N-alkyl substituted succinamates.

C. Ampholytic Surfactants

Ampholytic surfactants can be broadly described as aliphatic derivatives of secondary or tertiary amines, or aliphatic derivatives of heterocyclic secondary and tertiary amines in which the aliphatic radical can be straight chain or branched and wherein one of the aliphatic substituents contains from about 8 to 18 carbon atoms and at least one contains an anionic water-solubilizing group, e.g. carboxy, sulfonate, sulfate. See U.S. Pat. No. 3,929,678 to Laughlin et al., issued Dec. 30, 1975 at column 19, lines 18-35 (herein incorporated by reference) for examples of ampholytic surfactants.

D. Zwitterionic Surfactants

Zwitterionic surfactants can be broadly described as derivatives of secondary and tertiary amines, derivatives of heterocyclic secondary and tertiary amines, or derivatives of quaternary ammonium, quaternary phosphonium or tertiary sulfonium compounds. See U.S. Pat. No. 3,929,678 to Laughlin et al., issued Dec. 30, 1975 at column 19, line 38 through column 22, line 48 (herein incorporated by reference) for examples of zwitterionic surfactants.

E. Cationic Surfactants

Cationic surfactants can also be included in detergent compositions of the present invention. Suitable cationic surfactants include the quaternary ammonium surfactants having the formula:

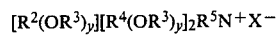

wherein $R^2$ is an alkyl or alkyl benzyl group having from about 8 to about 18 carbon atoms in the alkyl chain; each $R^3$ is selected from the group consisting of $-CH_2CH_2-$, $-CH_2CH(CH_3)-$, $-CH_2CH(CH_2OH)-$, $-CH_2CH_2CH_2-$, and mixtures thereof; each $R^4$ is selected from the group consisting of $C_1-C_4$ alkyl, $C_1-C_4$ hydroxyalkyl, benzyl, ring structures formed by joining the two $R^4$ groups, $-CH_2CHOH-CHOHCOR^6CHOHCH_2OH$ wherein $R^6$ is any hexose or hexose polymer having a molecular weight less than about 1000, and hydrogen when y is not 0; $R^5$ is the same as $R^4$ or is an alkyl chain wherein the total number of carbon atoms of $R^2$ plus $R^5$ is not more than about 18; each y is from 0 to about 10 and the sum of the y values is from 0 to about 15; and X is any compatible anion.

Preferred of the above are the alkyl quaternary ammonium surfactants, especially the mono-long chain alkyl surfactants described in the above formula when $R^5$ is selected from the same groups as $R^4$. The most preferred quaternary ammonium surfactants are the chloride, bromide and methylsulfate $C_8-C_{16}$ alkyl trimethylammonium salts, $C_8-C_{16}$ alkyl di(hydroxyethyl)-methylammonium salts, the $C_8-C_{16}$ alkyl hydroxyethyl-dimethylammonium salts, and $C_8-C_{16}$ alkyloxypropyl trimethylammonium salts. Of the above, decyl trimethylammonium methylsulfate, lauryl trimethylammonium chloride, myristyl trimethylammonium bromide and coconut trimethylammonium chloride and methylsulfate are particularly preferred.

Detergent Builders

Detergent compositions of the present invention can optionally comprise inorganic or organic detergent builders to assist in mineral hardness control. These builders can comprise from 0 to about 80% by weight of the composition. When included, these builders typically comprise up to about 60% by weight of the detergent composition. Built liquid formulations preferably comprise from about 10 to about 25% detergent builder while built granular formulations preferably comprise from about 10 to about 50% by weight detergent builder.

Suitable detergent builders include crystalline aluminosilicate ion exchange materials having the formula:

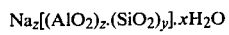

wherein z and y are at least about 6, the mole ratio of z to y is from about 1.0 to about 0.5; and x is from about 10 to about 264. Amorphous hydrated aluminosilicate materials useful herein have the empirical formula

wherein M is sodium, potassium, ammonium or substituted ammonium, z is from about 0.5 to about 2; and y is 1; this material having a magnesium ion exchange capacity of at least about 50 milligram equivalents of $CaCO_3$ hardness per gram of anhydrous aluminosilicate.

The aluminosilicate ion exchange builder materials are in hydrated form and contain from about 10% to about 28% of water by weight if crystalline, and potentially even higher amounts of water if amorphous. Highly preferred crystalline aluminosilicate ion exchange materials contain from about 18% to about 22% water in their crystal matrix. The preferred crystalline aluminosilicate ion exchange materials are further characterized by a particle size diameter of from about 0.1 micron to about 10 microns. Amorphous materials are often smaller, e.g., down to less than about 0.01 micron. More preferred ion exhange materials have a particle size diameter of from about 0.2 micron to about 4 microns. The term "particle size diameter" represents the average particle size diameter of a given ion exchange material as determined by conventional analytical techniques such as, for example, microscopic determination utilizing a scanning electron microscope. The crystalline aluminosilicate ion exchange materials are usually further characterized by their calcium ion exchange capacity, which is at least about 200 mg. equivalent of $CaCO_3$ water hardness/g. of aluminosilicate, calculated on an anhydrous basis, and which generally is in the range of from about 300 mg. eq./g. to about 352 mg. eq./g. The aluminosilicate ion exchange materials are still further characterized by their calcium ion exchange rate which is at least about 2 grains $Ca^{++}$/gallon/minute/gram/gallon of aluminosilicate (anhydrous basis), and generally lies within the range of from about 2 grains/gallon/minute/gram/gallon to about 6 grains/gallon/minute/gram/gallon, based on calcium ion hardness. Optimum aluminosilicates for builder purposes exhibit a calcium ion exchange rate of at least about 4 grains/gallon/minute/gram/gallon.

The amorphous aluminosilicate ion exchange materials usually have a $Mg^{++}$ exchange capacity of at least about 50 mg. eq. $CaCO_3$/g. (12 mg. $Mg^{++}$/g.) and a $Mg^{++}$ exchange rate of at least about 1 grain/gallon/minute/gram/gallon. Amorphous materials do not exhibit an observable diffraction pattern when examined by Cu radiation (1.54 Angstrom Units).

Useful aluminosilicate ion exchange materials are commercially available. These aluminosilicates can be crystalline or amorphous in structure and can be naturally-occurring aluminosilicates or synthetically derived. A method for producing aluminosilicate ion exchange materials is disclosed in U.S. Pat. No. 3,985,669 to Krummel, et al. issued Oct. 12, 1976 (herein incorporated by reference). Preferred synthetic crystalline aluminosilicate ion exchange materials useful herein are available under the designations Zeolite A, Zeolite P (B), and Zeolite X. In an especially preferred embodiment, the crystalline aluminosilicate ion exchange material has the formula,

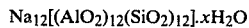

$Na_{12}[(AlO_2)_{12}(SiO_2)_{12}] \cdot xH_2O$ wherein x is from about 20 to about 30, especially about 27.

Other examples of detergency builders include the various water-soluble, alkali metal, ammonium or substituted ammonium phosphates, polyphosphates, phosphonates, polyphosphonates, carbonates, silicates, borates, polyhydroxysulfonates, polyacetates, carboxylates, and polycarboxylates. Preferred are the alkali metal, especially sodium, salts of the above.

Specific examples of inorganic phosphate builders are sodium and potassium tripolyphosphate, pyrophosphate, polymeric metaphate having a degree of polymerization of from about 6 to 21, and orthophosphate. Examples of polyphosphonate builders are the sodium and potassium salts of ethylene-1,1-diphosphonic acid, the sodium and potassium salts of ethane 1-hydroxy-1,1-diphosphonic acid and the sodium and potassium salts of ethane, 1,1,2-triphosphonic acid. Other phosphorus builder compounds are disclosed in U.S. Pat. Nos. 3,159,581; 3,213,030; 3,422,021; 3,422,137; 3,400,176 and 3,400,148 (all herein incorporated by reference).

Examples of nonphosphorus, inorganic builders are sodium and potassium carbonate, bicarbonate, sesquicarbonate, tetraborate decahydrate, and silicate having a mole ratio of $SiO_2$ to alkali metal oxide of from about 0.5 to about 4.0, preferably from about 1.0 to about 2.4.

Useful water-soluble, nonphosphorus organic builders include the various alkali metal, ammonium and substituted ammonium polyacetates, carboxylates, polycarboxylates and polyhydroxysulfonates. Examples of polyacetate and polycarboxylate builders are the sodium, potassium lithium, ammonium and substituted ammonium salts of ethylenediamine tetraacetic acid, nitrilotriacetic acid, oxydisuccinic acid, mellitic acid, benzene polycarboxylic acids, and citric acid.

Highly preferred polycarboxylate builders are disclosed in U.S. Pat. No. 3,308,067 to Diehl, issued Mar. 7, 1967 (herein incorporated by reference). Such materials include the water-soluble salts of homo- and copolymers of aliphatic carboxylic acids such as maleic acid, itaconic acid, mesaconic acid, fumaric acid, aconitic acid, citraconic acid and methylenemalonic acid.

Other builders include the carboxylated carbohydrates disclosed in U.S. Pat. No. 3,723,322 to Diehl issued Mar. 28, 1973 (herein incorporated by reference).

Other useful builders are sodium and potassium carboxymethyloxymalonate, carboxymethyloxysuccinate, cis-cyclohexanehexacarboxylate, cis-cyclopentanetetracarboxylate phloroglucinol trisulfonate, water-soluble polyacrylates (having molecular weights of from about 2,000 to about 200,000 for example), and the copolymers of maleic anhydride with vinyl methyl ether or ethylene.

Other suitable polycarboxylates are the polyacetal carboxylates disclosed in U.S. Pat. No. 4,144,226, to Crutchfield et al. issued Mar. 13, 1979, and U.S. Pat. No. 4,246,495, to Crutchfield et al., issued Mar. 27, 1979 (both herein incorporated by reference). These polyacetal carboxylates can be prepared by bringing together under polymerization conditions an ester of glyoxylic acid and a polymerization initiator. The resulting polyacetal carboxylate ester is then attached to chemically stable end groups to stabilize the polyacetal carboxylate against rapid depolymerization in alkaline solution, converted to the corresponding salt, and added to a surfactant.

Other useful detergency builder materials are the "seeded builder" compositions disclosed in Belgian Pat. No. 798,856, issued Oct. 29, 1973, (herein incorporated by reference). Specific examples of such seeded builder mixtures are: 3:1 wt. mixtures of sodium carbonate and calcium carbonate having 5 micron particle diameter; 2.7:1 wt. mixtures of sodium sesquicarbonate and calcium carbonate having a particle diameter of 0.5 microns; 20:1 wt. mixtures of sodium sesquicarbonate and calcium hydroxide having a particle diameter of 0.01 micron; and a 3:3:1 wt. mixture of sodium carbonate, sodium aluminate and calcium oxide having a particle diameter of 5 microns.

Other Optional Detergent Ingredients

Other optional ingredients which can be included in detergent compositions of the present invention, in their conventional art-established levels for use (i.e., from 0 to about 20%), include solvents, bleaching agents, bleach activators, soil-suspending agents, corrosion inhibitors, dyes, fillers, optical brighteners, germicides, pH adjusting agents (monoethanolamine, sodium carbonate, sodium hydroxide, etc.), enzymes, enzyme-stabilizing agents, perfumes, fabric softening components, static control agents, and the like.

Detergent Formulations

Granular formulations embodying the detergent compositions of the present invention can be formed by conventional techniques, i.e., by slurrying the individual components in water and then atomizing and spraydrying the resultant mixture, or by pan or drum granulation of the ingredients. Granular formulations preferably comprise from about 10 to about 30% detergent surfactant, usually anionic.

Liquid formulations embodying the detergent compositions can be built or unbuilt. If unbuilt, these compositions conventionally contain approximately 15 to 50% total surfactant, from 0 to 10% of an organic base such as a mono-, di-, or tri-alkanol amine, a neutralization system such as an alkali metal hydroxide and a lower primary alcohol such as ethanol or isopropanol, and approximately 20 to 80% water. Such compositions are normally homogeneous single phase liquids of low viscosity (approximately 100 to 150 centipoise at 75° F.).

Built liquid detergent compositions can be in the form of single phase liquids provided that the builder is solubilized in the mixture at its level of use. Such liquids conventionally contain 10 to 25% total surfactant, 10 to 25% builder which can be organic or inorganic, 3 to 10% of a hydrotrope system and 40 to 77% water. Liquids of this type also have a low viscosity (100 to 150 centipoise at 75° F.). Built liquid detergents incorporating components that form heterogenous mixtures (or levels of builder that cannot be completely dissolved) can also comprise detergent compositions of the present invention. Such liquids conventionally employ viscosity modifiers to produce systems having plastic shear characteristics to maintain stable dispersions and to prevent phase separation or solid settlement.

Near Neutral Wash pH Detergent Formulations

While the detergent compositions of the present invention are operative within a wide range of wash pHs (e.g. from about 5 to about 12), they are particularly suitable when formulated to provide a near neutral wash pH, i.e. an initial pH of from about 6.0 to about 8.5 at a concentration of from about 0.1 to about 2% by weight in water at 20° C. Near neutral wash pH formulations are better for enzyme stability and for preventing stains from setting. In such formulations, the pH is preferably from about 7.0 to about 8.5, and more preferably from about 7.5 to about 8.0.

Preferred near neutral wash pH detergent formulations are disclosed in U.S. application Ser. No. 380,988 to J. H. M. Wertz and P. C. E. Goffinet, filed May 24, 1982. These preferred formulations comprise:

(a) from about 2 to about 60% (preferably from about 10 to about 25%) by weight of an anionic synthetic surfactant as previously defined;
(b) from about 0.25 to about 12% (preferably from about 1 to about 4%) by weight of a cosurfactant selected from the group consisting of:
 (i) quaternary ammonium surfactants having the formula:

$$[R^2(OR^3)_y][R^4(OR^3)_y]_2R^5N^+X^-$$

wherein $R^2$, each $R^3$, $R^4$, $R^5$, X and y are as previously defined;
 (ii) diquaternary ammonium surfactants having the formula:

$$[R^2(OR^3)_y][R^4(OR^3)_y]_2N^+R^3N^+R^5[R^4(OR^3)_y]_2(X^-)_2$$

wherein $R^2$, $R^3$, $R^4$, y and X are as defined above; particularly preferred are the $C_8$–$C_{16}$ alkyl pentamethylethylenediamine chloride, bromide and methylsulfate salts;
 (iii) amine surfactants having the formula:

$$[R^2(OR^3)_y][R^4(OR^3)_y]R^5N$$

wherein $R^2$, $R^3$, $R^4$, $R^5$ and y are as defined above; particularly preferred are the $C_{12}$–$C_{16}$ alkyl dimethyl amines;
 (iv) diamine surfactants having the formula:

$$[R^2(OR^3)_y][R^4(OR^3)_y]NR^3NR^5[R^4(OR^3)_y]$$

wherein $R^2$, $R^3$, $R^4$, $R^5$ and y are as defined above; particularly preferred are the $C_{12}$–$C_{16}$ alkyl dimethyl diamines;
 (v) amine oxide surfactants having the formula:

$$[R^2(OR^3)_y][R^4(OR^3)_y]R^5N \rightarrow O$$

wherein $R^2$, $R^3$, $R^4$, $R^5$ and y are as defined above; particularly preferred are the $C_{12}$–$C_{16}$ alkyldimethyl amine oxides; and
 (vi) di(amine oxide) surfactants having the formula:

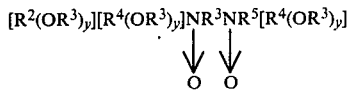

wherein $R^2$, $R^3$, $R^4$, $R^5$ and y are as defined above; preferred are the $C_{12}$–$C_{16}$ alkyl trimethylethylene di(amine oxides) and
(c) from about 5% to about 40% by weight (preferably 7 to about 30% by weight, and most preferably from about 10 to 20% by weight) of a fatty acid containing from about 10 to about 22 carbon atoms (preferably a $C_{10}$–$C_{14}$ saturated fatty acid or mixture thereof); the mole ratio of the anionic surfactant to the cosurfactant being at least 1 and preferably from about 2:1 to about 20:1.

Such compositions also preferably contain from about 3 to about 15% by weight of an ethoxylated alcohol or ethoxylated alkyl phenol (nonionic surfactants) as previously defined. Highly preferred compositions of this type also preferably contain from about 2 to about 10% by weight of citric acid and minor amounts (e.g., less than about 20% by weight) of neutralizing agents, buffering agents, phase regulants, hydrotropes, enzymes, enzyme stabilizing agents, polyacids, suds regulants, opacifiers, anti-oxidants, bactericides, dyes, perfumes and brighteners, such as those described in U.S. Pat. No. 4,285,841 to Barrat et al., issued Aug. 25, 1981 (herein incorporated by reference).

Specific Embodiments of Detergent Compositions According to the Present Invention The following embodiments illustrate, but are not limiting of, detergent compositions of the present invention:

A granular detergent composition is as follows:

| Component | Wt. % |
| --- | --- |
| Polyurethane of Example 3 | 1.0 |
| Sodium $C_{14}$–$C_{15}$ alkylethoxysulfate | 10.7 |
| $C_{13}$ linear alkyl benzene sulfonic acid | 4.3 |
| $C_{12}$–$C_{14}$ alkylpolyethoxylate (6) | 0.5 |
| Sodium toluene sulfonate | 1.0 |

| Component | Wt. % |
| --- | --- |
| Sodium tripolyphosphate | 32.9 |
| Sodium carbonate | 20.3 |
| Sodium silicate | 5.8 |
| Minors and water | Balance to 100 |

The components are added together with continuous mixing to form an aqueous slurry which is then spray dried to form the composition. Instead of the polyurethane, the amine oxides of Examples 1 or 2, the random copolymer of Example 4, the PEA of Example 5a, the PEI of Example 5b or the diallylamine polymer of Example 6 can be substituted therefor.

Embodiment II

A liquid detergent composition is as follows:

| Component | Wt. % |
| --- | --- |
| Random copolymer of Example 4 | 1.0 |
| Sodium $C_{14}$—$C_{15}$ alkyl polyethoxy (2.5) sulfate | 8.3 |
| $C_{12}$—$C_{14}$ alkyl dimethyl amine oxide | 3.3 |
| Sodium toluene sulfonate | 5.0 |
| Monoethanolamine | 2.3 |
| Sodium nitrilotriacetate | 18.2 |
| Minors and water | Balance to 100 |

The components are added together with continuous mixing to form the composition. Instead of the random copolymer, the polyurethane of Example 3, the PEA of Example 5a, the PEI of Example 5b or the diallylamine polymer of Example 6 can be substituted therefor.

Embodiments III and IV

Liquid detergent compositions are as follows:

| | Wt. % | |
| Component | III | IV |
| --- | --- | --- |
| HMDA Oxide of Example 2b | 1.5 | 1.5 |
| $C_{14}$—$C_{15}$ alkylethoxysulfuric acid | 10.8 | — |
| $C_{14}$—$C_{15}$ alkylpolyethoxy (2.25) sulfuric acid | — | 10.8 |
| $C_{13}$ linear alkylbenzene sulfonic acid | 7.2 | 7.2 |
| $C_{12}$ alkyl trimethylammonium chloride | 1.2 | 1.2 |
| $C_{12}$—$C_{13}$ alcohol polyethoxylate (6.5) | 6.5 | 6.5 |
| Coconut fatty acid | 15.0 | 15.0 |
| Citric acid monohydrate | 6.9 | 4.0 |
| Diethylenetriamine pentaacetic acid | 0.9 | 0.9 |
| Protease enzyme | 0.8 | 0.8 |
| Amylase enzyme | 0.3 | 0.3 |
| Monoethanolamine | 13.6 | 2.0 |
| Triethanolamine | 3.0 | 4.0 |
| Sodium hydroxide | — | 2.0 |
| Potassium hydroxide | — | 2.8 |
| 1,2-Propanediol | 5.0 | 5.0 |
| Ethanol | 3.0 | 7.0 |
| Sodium formate | 1.0 | 1.0 |
| Sodium toluene sulfonate | 5.0 | — |
| Minors and water | Balance to 100 | |

Embodiment IV is prepared by adding the components together with continuous mixing, in the following order to produce a clear liquid: a paste premix of the alkylbenzene sulfonic acid, 0.9 parts of the sodium hydroxide, propylene glycol, and 2.3 parts of the ethanol; a paste premix of the alkylpolyethoxysulfuric acid, 1.1 parts of the sodium hydroxide and 3.1 parts of the ethanol; alcohol polyethoxylate; premix of monoethanolamine, triethanolamine and brighteners, 1.5 parts potassium hydroxide; balance of the ethanol; citric acid; formate; 1.4 parts potassium hydroxide; fatty acid; pentaacetic acid; alkyl trimethylammonium chloride; adjust pH to about 8.4 with potassium hydroxide, water or citric acid; enzymes; HMDA oxide (50% aqueous solution); and perfume. Embodiment III can be prepared in a similar manner. Instead of the HMDA oxide, the polyurethane of Example 3, the random copolymer of Example 4, the PEI of Example 5b or the diallylamine polymer of Example 6 can be substituted therefor.

Embodiment V

A liquid detergent composition is as follows:

| Component | Wt. % |
| --- | --- |
| PEA of Example 5a | 1.0 |
| Sodium $C_{12}$ alkylpolyethoxy (3) sulfate | 12.6 |
| $C_{12}$—$C_{13}$ alcohol polyethoxylate (6.5) | 23.4 |
| Monoethanolamine | 2.0 |
| Ethanol | 9.0 |
| Citric acid monohydrate | 0.8 |
| Minors and water | Balance to 100 |

The components are added together with continuous mixing to form the composition. Instead of the PEA, the amine oxides of Examples 1 or 2, the polyurethane of Example 3, the random copolymer of Example 4, the PEI of Example 5b or the diallylamine polymer of Example 6 can be substituted therefor.

Bleach Compatibility of Ethoxylated Amine Oxide Polymers Relative to Ethoxylated Amine Polymers, Based on Anti-Redeposition Properties

A. Experimental Method

Anti-redeposition comparisons were conducted in a 5 pot Automatic Miniwasher (AMW) employing 7 grain hardness water and temperature of 95° F. Test swatches were washed for 10 minutes and rinsed twice with water (7 grains hardness) at 75° F. for 2 minutes.

One wash employed 2000 ppm of a control liquid detergent composition containing the following surfactants:

| Surfactant | Amount (%) |
| --- | --- |
| Sodium $C_{14}$—$C_{15}$ alkyl ethoxysulfate | 10.8 |
| $C_{13}$ linear alkylbenzene sulfonic acid | 7.2 |
| $C_{12}$—$C_{13}$ alcohol polyethoxylate (6.5) | 6.5 |
| $C_{12}$ alkyl trimethylammonium chloride | 1.2 |

A second wash used the same detergent composition but also contained an ethoxylated amine polymer at 20 ppm. A third wash used the same detergent composition but also contained an ethoxylated amine oxide polymer of the present invention at 20 ppm. None of the detergent compositions contained optical brighteners.

After the AMW pots were filled with 6 liters of water each, the detergent composition to be tested was added and agitated for 2 minutes. In those tests involving chlorine bleach, 210 ppm NaOCl (200 ppm chlorine) was added at the same time as the detergent composition. A background soil mixture (200 ppm artificial body soil, 100 ppm vacuum cleaner soil and 200 ppm clay soil) was then added and agitated for an additional 3 minutes. Three 5 inch square test swatches (50% polyester/50% cotton T-shirt material) were then added, along with two 80% cotton/20% polyester terry clothes and two 11 inch square swatches of 100% polyester knit fabric. The 10 minute wash cycle commenced at this point.

Following the rinse cycle, the test swatches were dried in a mini-dryer. Hunter color coordinates (L, a and b) were then determined for the three test swatches. Anti-redeposition performance (ARD) was then calculated according to the following equation:

$$ARD = \frac{7L^2 - 40Lb}{700}$$

The ARD values for the three test swatches were then averaged.

B. Test Results

The results from testing the anti-redeposition performance of the control, ethoxylated amine polymer and ethoxylated amine oxide polymer compositions (with and without NaOCl) is shown in the following Table:

| Composition | ARD (w/NaOCl) | ARD (w/o NaOCl) |
|---|---|---|
| Control | 104.5 | 103.8 |
| PEA 189 E$_{15}$* | 105.8 | 119.2 |
| PEA 189 E$_{15}$ Oxide** | 109.6 | 119.4 |

*Polyethyleneamine (M.W. 189), degree of ethoxylation of 15
**Polyethyleneamine (M.W. 189), degree of ethoxylation of 15, 90.7% amine oxide groups.

As can be seen in the above Table, the ethoxylated amine oxide polymer of the present invention was more bleach compatible than the ethoxylated amine polymer.

What is claimed is:

1. A water-soluble amine oxide having clay soil removal/anti-redeposition properties selected from the group consisting of:

(1) ethoxylated monoamine oxides having formula I:

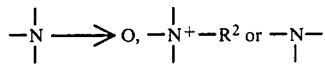

(2) ethoxylated amine oxides having formulas IIA, IIB or IIC:

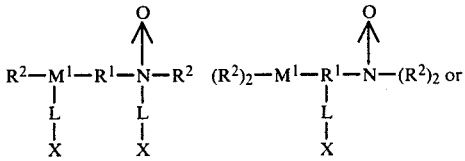

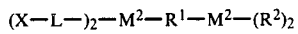

IIC wherein M$^1$ is an

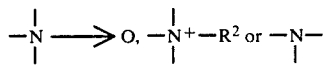

group; each M$^2$ is an

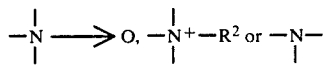

group, and at least one M$^2$ is an

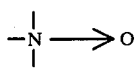

group;

(3) ethoxylated amine oxides having formula III:

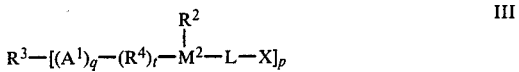

(4) ethoxylated amine oxide polymers which comprise a polymer backbone, at least 2M$^3$ groups and at least one L—X group, wherein M$^3$ is an amine oxide group attached to or integral with the backbone; and L connects groups M$^3$ and X, or connects group X to the polymer backbone; and (5) mixtures thereof; wherein A$^1$ is

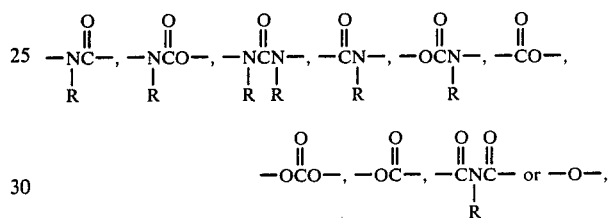

—O—, R is H or C$_1$–C$_4$ alkyl or hydroxyalkyl; R$^1$ is C$_2$–C$_{12}$ alkylene, hydroxyalkylene, alkenylene, arylene or alkarylene, or a C$_2$–C$_3$ oxyalkylene moiety having from 2 to about 20 oxyalkylene units provided that no O—N bonds are formed; each R$^2$ is C$_1$–C$_4$ alkyl or hydroxyalkyl, the moiety —L—X, or two R$^2$ together form the moiety —(CH$_2$)$_r$—A$^2$—(CH$_2$)$_s$—, wherein A$^2$ is —O— or —CH$_2$—, r is 1 or 2, s is 1 or 2 and r+s is 3 or 4; R$^3$ is a substituted C$_3$–C$_{12}$ alkyl, hydroxyalkyl, alkenyl, aryl or alkaryl group having p substitution sites; R$^4$ is C$_1$–C$_{12}$ alkylene, hydroxyalkylene, alkenylene, arylene or alkarylene, or a C$_2$–C$_3$ oxyalkylene moiety having from 2 to about 20 oxyalkylene units provided that no O—N bonds are formed; X is a nonionic group selected from the group consisting of H, C$_1$–C$_4$ alkyl or hydroxyalkyl ester groups, C$_1$–C$_4$ alkyl or hydroxyalkyl ether groups, and mixtures thereof, or a mixture of said nonionic group and an anionic group selected from the group consisting of COO$^-$, PO$_3^{3-}$$^{1\,2}$ and SO$_3^-$; L is a hydrophilic chain which contains the polyoxyalkylene moiety —[(R$^5$O)$_m$(CH$_2$CH$_2$O)$_n$]—, wherein R$^5$ is C$_3$–C$_4$ alkylene or hydroxyalkylene, and m and n are numbers such that the moiety —(CH$_2$CH$_2$O)$_n$— comprises at least about 50% by weight of said polyoxyalkylene moiety; n is at least about 12 for said monoamine oxides of formula 1, is at least about 6 for said amine oxides of formulas IIA, IIB or IIC, is at least 3 for said amine oxides of formula III and is at least about 12 for said amine oxide polymers; p is from 3 to 8; q is 1 or 0; t is 1 or 0, provided that t is 1 when a is 1.

2. An amine oxide according to claim 1 which is a monoamine oxide of formula I.

3. An amine oxide according to claim 2 wherein m is 0 and n is at least about 15.

4. An amine oxide according to claim 1 which is an amine oxide of formulas IIA, IIB, IIC or III and wherein each $R^2$ is the moiety —L—X.

5. An amine oxide according to claim 4 wherein m and n are numbers such that the moiety —$(CH_2CH_2O)_n$— comprises at least about 85% by weight of said polyoxyalkylene moiety.

6. An amine oxide according to claim 5 wherein X is a nonionic group.

7. An amine oxide according to claim 6 wherein X is H.

8. An amine oxide according to claim 7 which is an amine oxide of formulas IIA, IIB or IIC.

9. An amine oxide according to claim 8 wherein $R^1$ is $C_2$-$C_6$ alkylene.

10. An amine oxide according to claim 9 wherein $R^1$ is $C_2$-$C_3$ alkylene.

11. An amine oxide according to claim 9 wherein $M^1$ and each $M^2$ are an

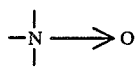

group.

12. An amine oxide according to claim 11 wherein m is 0 and n is at least about 12.

13. An amine oxide according to claim 7 which is an amine oxide of formula III.

14. An amine oxide according to claim 13 wherein $R^3$ is a substituted $C_3$-$C_6$ alkyl, hydroxyalkyl or aryl group; $A^1$ is

and p is from 3 to 6.

15. An amine oxide according to claim 14 wherein each $M^2$ is an

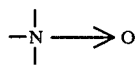

group.

16. An amine oxide according to claim 15 wherein m is 0 and n is at least about 12.

17. An amine oxide according to claim 1 which is an amine oxide polymer.

18. An amine oxide polymer according to claim 17 wherein said backbone is selected from the group consisting of the polyurethanes, the polyesters, the polyethers, the polyamides, the polyimides, the polyacrylates, the polyacrylamides, the polyvinylethers, the polyalkylenes, the polyalkarylenes, the polyalkyleneamines, the polyalkyleneimines, the polyvinylamines, the polyallylamines, the polydiallylamines, the polyvinylpyridines, the polyaminotriazoles, polyvinyl alcohol, the aminopolyureylenes and mixtures thereof.

19. An amine oxide polymer according to claim 18 wherein the ratio of groups $M^3$ to groups X is from about 1:1 to about 1:5.

20. An amine oxide polymer according to claim 19 wherein units containing groups $M^3$ and L—X comprise from about 50 to 100% of the polymer.

21. An amine oxide polymer according to claim 20 wherein the number of groups $M^3$ and L—X are each from about 3 to about 40.

22. An amine oxide polymer according to claim 21 wherein m and n are numbers such that the moiety —$(CH_2CH_2O)_n$— comprises at least about 85% by weight of said polyoxyalkylene moiety.

23. An amine oxide polymer according to claim 22 wherein m is 0.

24. An amine oxide polymer according to claim 23 wherein X is said nonionic group.

25. An amine oxide polymer according to claim 24 wherein X is H.

26. An amine oxide polymer according to claim 17 which comprises united selected from those having formulas IV, V and VI:

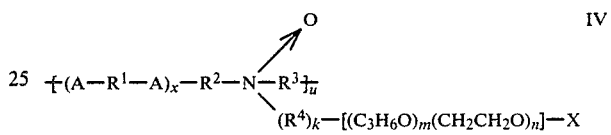

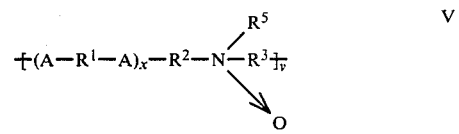

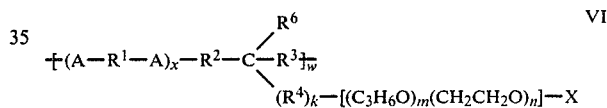

wherein A is

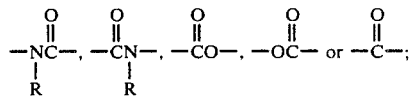

x is 0 or 1; R is H or $C_1$-$C_4$ alkyl or hydroxyalkyl; $R^1$ is $C_2$-$C_{12}$ alkylene, hydroxyalkylene, alkenylene, cycloalkylene, arylene or alkarylene, or a $C_2$-$C_3$ oxyalkylene moiety having from 2 to about 20 oxyalkylene units provided that no O—O or O—N bonds are formed with A; when x is 1, $R^2$ is —$R^4$— except when A is

or is —$(OR^7)_y$— or —$OR^4$— provided that no O—O or N—O bonds are formed with A, and $R^3$ is —$R^5$— except when A is

or is —$(R^7O)$—$_y$ or —$R^4O$— provided that no O—O or O—N bonds are formed with A; when x is O, $R^2$ is —$(OR^7)_y$—, —$OR^4$—,

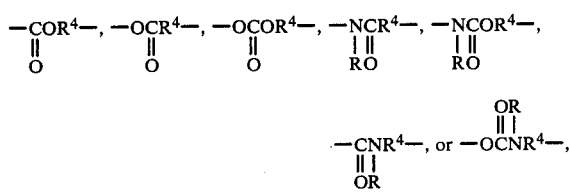

and $R^3$ is $—R^4—$; $R^4$ is $C_1$-$C_{12}$ alkylene, hydroxyalkylene, alkenylene, arylene, or alkarylene; $R^5$ is $C_1$-$C_4$ alkyl or hydroxyalkyl; $R^6$ is H, $C_1$-$C_4$ alkyl or hydroxyalkyl, or the moiety $—(R^4)_k—[(C_3H_6O)_m(CH_2CH_2O)_n—]—X$; $R^7$ is $C_2$-$C_3$ alkylene or hydroxyalkylene; X is H,

$—R^8$ or a mixture thereof, wherein $R^8$ is $C_1$-$C_4$ alkyl or hydroxyalkyl; k is 0 or 1; m and n are numbers such that the moiety $—(CH_2CH_2O)_n—$ comprises at least about 85% by weight of the moiety $—[(C_3H_6O)_m(CH_2CH_2O)_n]—$; m is from 0 to about 5; n is at least about 12; y is from 2 to about 20; the number of u, v and w are such that there are at least 2

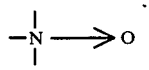

groups and at least 2 X groups.

27. An amine oxide polymer according to claim 26 wherein A is

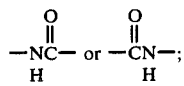

x is 1; $R^1$ is $C_2$-$C_6$ alkylene; $R^2$ is $—OR^4—$ or $—(OR^7—)_y—$; $R^3$ is $—R^4O—$ or $—(R^7O)_y—$; $R^4$ is $C_2$-$C_3$ alkylene; $R^5$ is methyl; $R^6$ is H or $C_1$-$C_3$ alkyl; $R^7$ is ethylene; X is H or methyl; k is 0; m is 0; y is from 2 to about 12.

28. An amine oxide polymer according to claim 27 wherein v and w are each 0, and u is from about 3 to about 40.

29. An amine oxide polymer according to claim 17 which comprises units selected from those having formulas VII, VIII and IX,

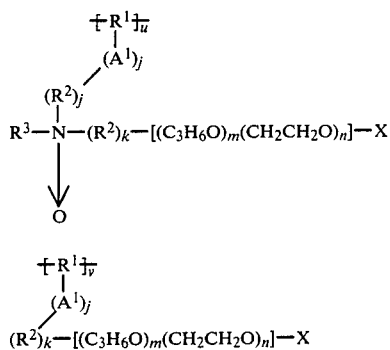

VII

VIII

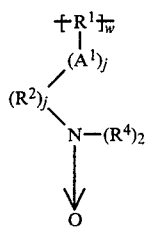

IX wherein $A^1$ is

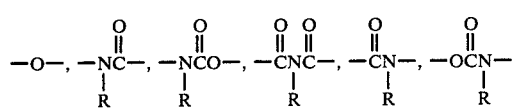

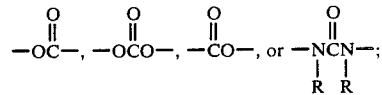

R is H or $C_1$-$C_4$ alkyl or hydroxyalkyl; $R^1$ is substituted $C_2$-$C_{12}$ alkylene, hydroxyalkylene, alkenylene, arylene or alkarylene, or $C_2$-$C_3$ oxyalkylene; each $R^2$ is $C_1$-$C_{12}$ alkylene, hydroxyalkylene, alkenylene, arylene or alkarylene; each $R^3$ is $C_1$-$C_4$ alkyl or hydroxyalkyl, or the moiety $—(R^2)_k—[(C_3H_6O)_m(CH_2CH_2O)_n]—X$; each $R^4$ is $C_1$-$C_4$ alkyl or hydroxyalkyl, or two $R^4$ together form the moiety $—(CH_2)_r—A^2—(CH_2)_s—$, wherein $A^2$ is $—O—$ or $—CH_2—$; X is H,

$—R^5$ or a mixture thereof, wherein $R^5$ is $C_1$-$C_4$ alkyl or hydroxyalkyl; j is 1 or 0; k is 1 or 0; m and n are numbers such that the moiety $—(CH_2CH_2O)_n—$ comprises at least about 85% by weight of the moiety $—[(C_3H_6O)_m(CH_2CH_2O)_n]—$; m is from 0 to about 5; n is at least about 12; r is 1 or 2, s is 1 or 2 and r+s is 3 or 4; the number of u, v and w are such that there are at least 2

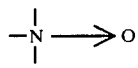

groups and at least 2 X groups.

30. An amine oxide polymer according to claim 29 wherein $A^1$ is

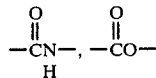

or $—O—$; $R^1$ is

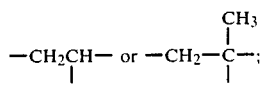

$R^2$ is $C_2$-$C_3$ alkylene; $R^3$ is methyl; each $R^4$ is methyl; X is H or methyl; j is 1; k is 0; m is 0.

31. An amine oxide polymer according to claim 1 wherein u is 0, and v and w are each from about 3 to about 40.

32. An amine oxide polymer according to claim 17 which comprises units selected from those having formulas X, XI and XII:

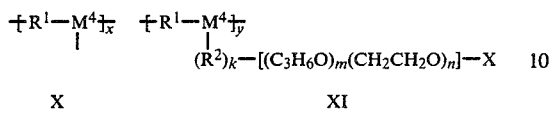

X           XI

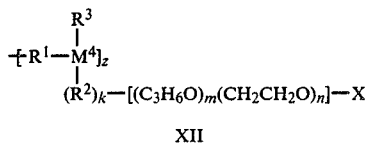

XII wherein $R^1$ is $C_2$–$C_{12}$ alkylene, hydroxyalkylene, alkenylene, cycloalkylene, arylene or alkarylene, or a $C_2$–$C_3$ oxyalkylene moiety having from 2 to about 20 oxyalkylene units provided that no O—N bonds are formed; $R^2$ is $C_1$–$C_{12}$ alkylene, hydroxyalkylene, alkenylene, arylene or alkarylene; $R^3$ is $C_1$–$C_4$ alkyl or hydroxyalkyl, or the moiety —$(R^2)_k$—$[(C_3H_6O)_m(CH_2CH_2O)_n]$—X; $M^4$ is an

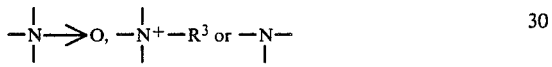

group; X is H,

—$R^4$ or a mixture thereof, wherein $R^4$ is $C_1$–$C_4$ alkyl or hydroxyalkyl; k is 1 or 0; m and n are numbers such that the moiety —$(CH_2CH_2O)_n$— comprises at least about 85% by weight of the moiety —$[(C_3H_6O)_m(CH_2CH_2O)]_n$—; m is from 0 to about 5; n is at least about 12; the number of x, y and z are such that there are at least 2 $M^4$ groups, at least 2

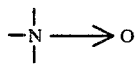

groups and at least 2 X groups.

33. An amine oxide polymer according to claim 32 wherein $R^1$ is $C_2$–$C_6$ alkylene; $R^3$ is methyl or the moiety —$(CH_2CH_2O)_n$—H; $R^4$ is methyl; X is H; k is 0; m is 0.

34. An amine oxide polymer according to claim 33 wherein $R^1$ is ethylene.

35. An amine oxide polymer according to claim 34 wherein $M^4$ is a mixture of from about 70 to 100%

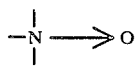

groups, and from 0 to about 30%

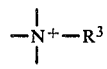

groups,

groups or mixtures thereof.

36. An amine oxide polymer according to claim 35 wherein x+y+z is from 2 to 9.

37. An amine oxide polymer according to claim 36 wherein x+y+z is at least 10.

38. An amine oxide polymer according to claim 17 which comprises units selected from those having formulas XVI and XVII:

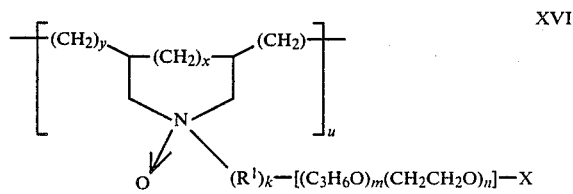

XVI

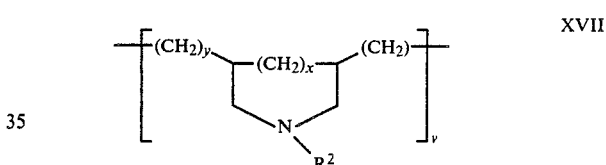

XVII wherein $R^1$ is $C_1$–$C_{12}$ alkylene, hydroxylalkylene, alkylene, arylene or alkarylene; $R^2$ is $C_1$–$C_4$ alkyl or hydroxyalkyl; X is H,

—$R^3$ or a mixture thereof, wherein $R^3$ is $C_1$–$C_4$ alkyl or hydroxyalkyl; k is 1 or 0; m and n are numbers such that the moiety —$(CH_2CH_2O)_n$— comprises at least about 85% by weight of the moiety $[(C_3H_6O)_m(CH_2CH_2O)_n]$—; m is from 0 to about 5; n is at least about 12; x is 1 or 0; y is 1 when x is 0, and 0 when x is 1; the number of u and v are such that there are at least 2

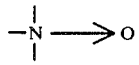

groups and at least 2 X groups.

39. An amine oxide polymer according to claim 38 wherein $R^2$ is methyl; X is H; k is 0 and x is 0.

40. An amine oxide polymer according to claim 39 wherein v is 0, and u is from 2 to about 40.

41. A water-soluble amine oxide polymer having clay soil removal anti-redeposition properties of formula XIII:

XIII

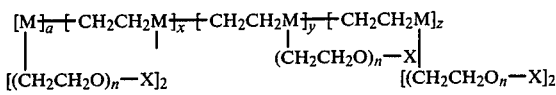

wherein M is an

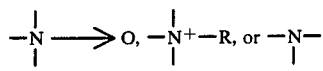

group; R is $C_1$-$C_4$ alkyl or hydroxyalkyl, or the moiety —$(CH_2CH_2O)_n$—X; X is H,

—$R^1$ or a mixture thereof, wherein $R^1$ is $C_1$-$C_4$ alkyl or hydroxyalkyl; n is at least about 3; a is 1 or 0; a, x, y and z are numbers such that there are at least two M groups, at least two

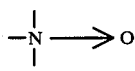

groups and at least two X groups.

42. An amine oxide polymer according to claim 41 wherein X is H.

43. An amine oxide polymer according to claim 42 wherein M is a mixture of from about 70 to 100%

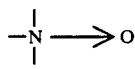

groups, and from 0 to about 30%

groups,

groups, or mixtures thereof.

44. An amine oxide polymer according to claim 43 wherein x+y+z is from 2 to 9.

45. An amine oxide polymer according to claim 43 wherein x+y+z is at least 10.

46. A detergent composition, which comprises:
(a) from about 1 to about 75% by weight of a nonionic, anionic, ampholytic, zwitterionic, or cationic detergent surfactant or mixture thereof; and
(b) from about 0.05 to about 95% by weight of a water-soluble amine oxide according to claim 1.

47. A composition according to claim 46 which comprises from about 0.1 to about 10% by weight of said amine oxide.

48. A composition according to claim 47 which comprises from about 1 to about 3% by weight of said amine oxide.

49. A composition according to claim 48 wherein said detergent surfactant is a nonionic surfactant, an anionic surfactant or a mixture thereof.

50. A composition according to claim 49 which further comprises from 0 to about 80% by weight of a detergent builder.

51. A composition according to claim 47 wherein said amine oxide is an amine oxide polymer having the general formula:

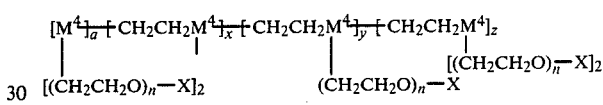

wherein $M^4$ comprises from about 70 to about 100%

groups, and from 0 to about 30%

groups,

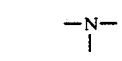

groups or mixtures thereof; X is H; a is 0 or 1; x+y+z is at least 2.

52. A composition according to claim 51 wherein x+y+z is from 2 to 9.

53. A composition according to claim 51 wherein x+y+z is at least 10.

* * * * *